(12) United States Patent
Wada et al.

(10) Patent No.: US 8,133,343 B2
(45) Date of Patent: Mar. 13, 2012

(54) DISPOSABLE WEARING ARTICLE

(75) Inventors: Takao Wada, Settsu (JP); Toyoshi Umebayashi, Settsu (JP); Shuhei Kurata, Settsu (JP); Mamoru Itani, Settsu (JP)

(73) Assignee: Zuiko Corporation (JP)

( * ) Notice: Subject to any disclaimer, the term of this patent is extended or adjusted under 35 U.S.C. 154(b) by 0 days.

(21) Appl. No.: 12/758,247

(22) Filed: Apr. 12, 2010

(65) Prior Publication Data

US 2010/0193111 A1    Aug. 5, 2010

Related U.S. Application Data

(62) Division of application No. 10/565,151, filed as application No. PCT/JP2004/011498 on Aug. 4, 2004, now Pat. No. 7,754,044.

(30) Foreign Application Priority Data

Aug. 6, 2003    (JP) ................................ 2003-288204

(51) Int. Cl.
*B32B 37/00*    (2006.01)
*B32B 37/16*    (2006.01)
*B32B 38/00*    (2006.01)
*B32B 38/04*    (2006.01)

(52) U.S. Cl. ........ 156/253; 156/250; 156/252; 156/256; 156/269

(58) Field of Classification Search .................. 156/250, 156/252, 253, 256, 269; 604/385.201, 385.21, 604/385.24, 385.25, 385.3
See application file for complete search history.

(56) References Cited

U.S. PATENT DOCUMENTS

| | | | | |
|---|---|---|---|---|
| 5,788,797 A * | 8/1998 | Herrin et al. | ................ | 156/73.1 |
| 5,858,151 A | 1/1999 | Igaue et al. | | |
| 6,755,808 B2 | 6/2004 | Balogh et al. | | |
| 6,827,804 B2 | 12/2004 | Otsubo et al. | | |
| 6,837,958 B2 | 1/2005 | Otsubo et al. | | |
| 6,911,106 B2 * | 6/2005 | Otsubo et al. | ................ | 156/229 |
| 6,979,380 B2 | 12/2005 | Thorson et al. | | |
| 7,160,408 B2 * | 1/2007 | Otsubo | ........................ | 156/163 |
| 7,407,557 B2 * | 8/2008 | Wada et al. | .................... | 156/226 |
| 2004/0035521 A1 * | 2/2004 | Nakakado et al. | ............ | 156/229 |
| 2006/0151093 A1 * | 7/2006 | Nakakado | ..................... | 156/164 |

FOREIGN PATENT DOCUMENTS

| | | |
|---|---|---|
| JP | 1-298202 | 12/1989 |
| JP | 3-176053 | 7/1991 |
| JP | 3015091 | 12/1999 |

(Continued)

*Primary Examiner* — Mark A Osele
*Assistant Examiner* — Christopher C Caillouet
(74) *Attorney, Agent, or Firm* — Gerald E. Hespos; Michael J. Porco

(57) ABSTRACT

A method comprising a step of manufacturing an elastic laminated body by laminating two webs and while inserting an elastic member in an extended state in a web length direction in between; a step of cutting the elastic laminated body in a length direction so that a concave portion and a convex portion appear alternately; a step of attaching a cover sheet to bridge between the concave portion and the convex portion of cut first elastic laminated body and second elastic laminated body, respectively; a step of widening the first elastic laminated body and the second elastic laminated body to which the cover sheet is attached; and a step of attaching an absorber onto the cover sheet, lessens the occurrence of wrinkles and creases produced when webs are cut, and eliminates a problem attributed to the occurrence of wrinkles and arising when an absorber is attached.

13 Claims, 27 Drawing Sheets

FOREIGN PATENT DOCUMENTS

| | | |
|---|---|---|
| JP | 2002-272781 | 9/2002 |
| JP | 2002-306534 | 10/2002 |
| JP | 2003-175066 | 6/2003 |
| WO | 03/039423 | 5/2003 |

* cited by examiner

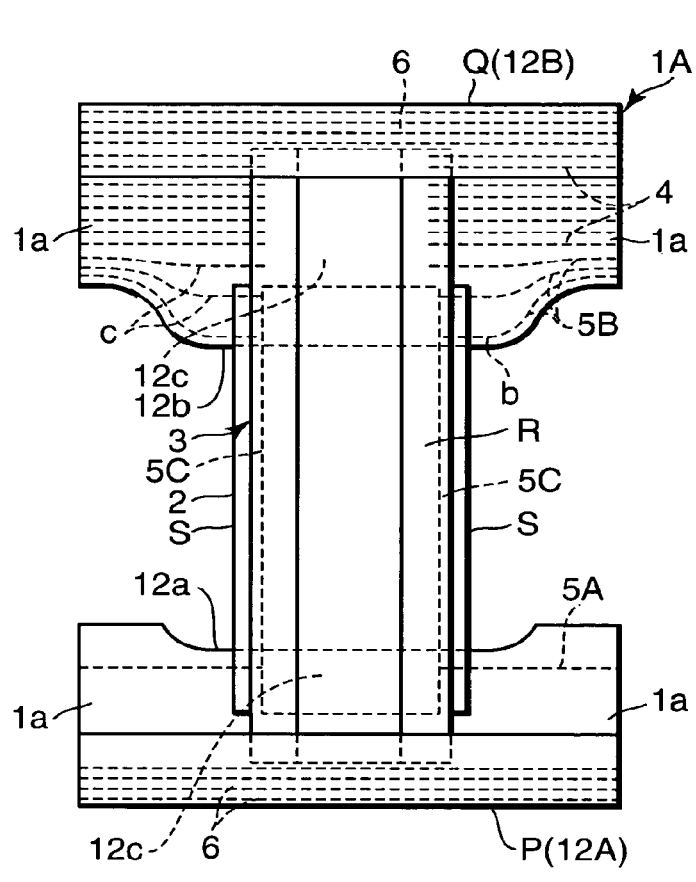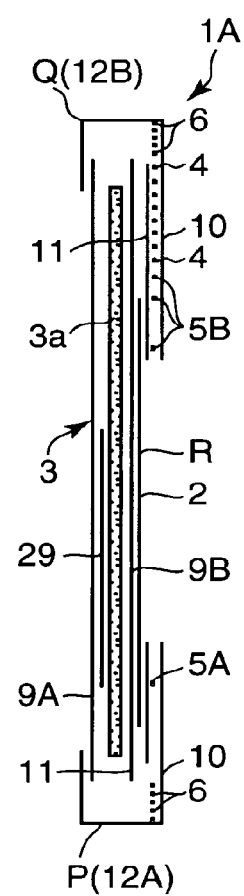

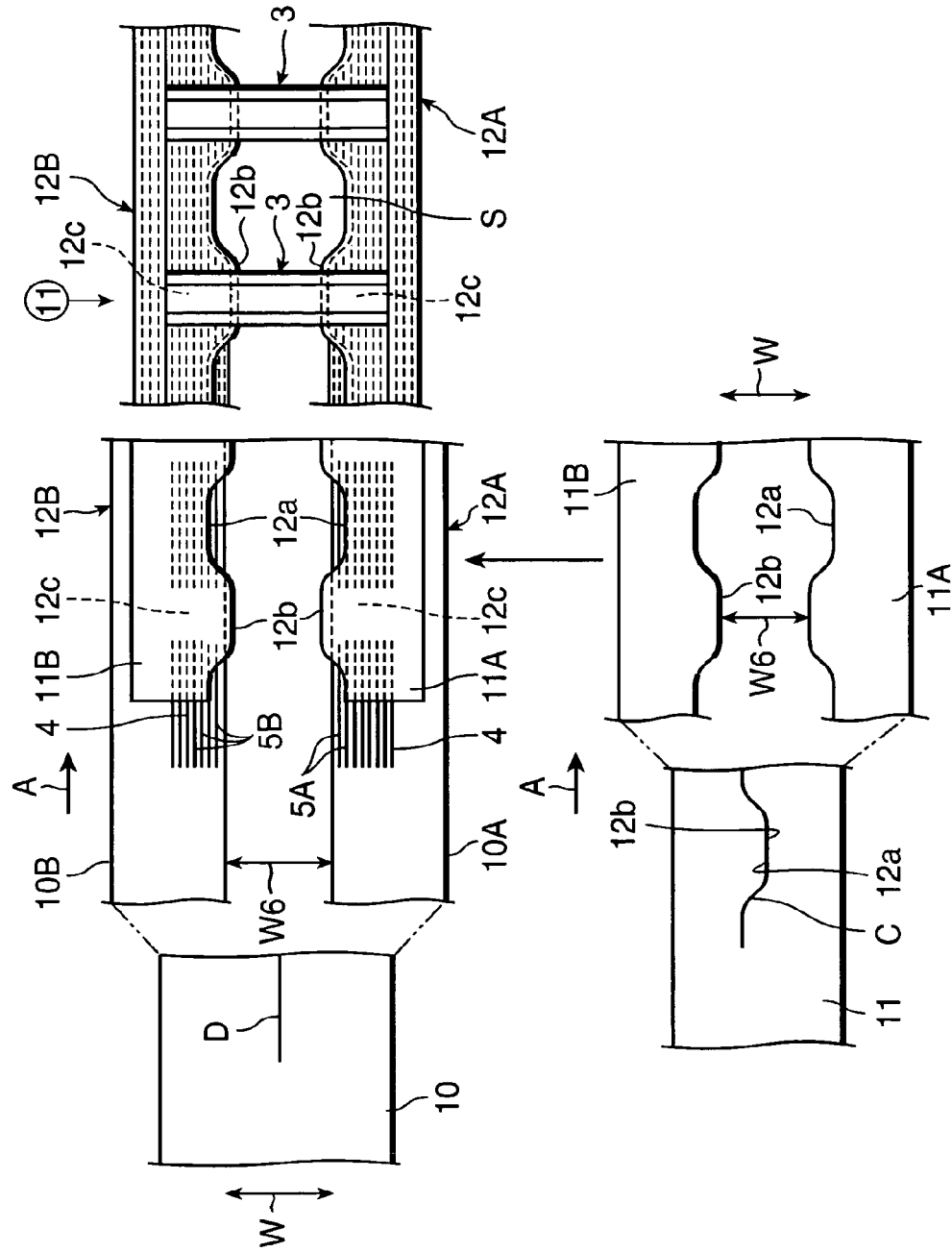

FIG.17A
FIG.17B
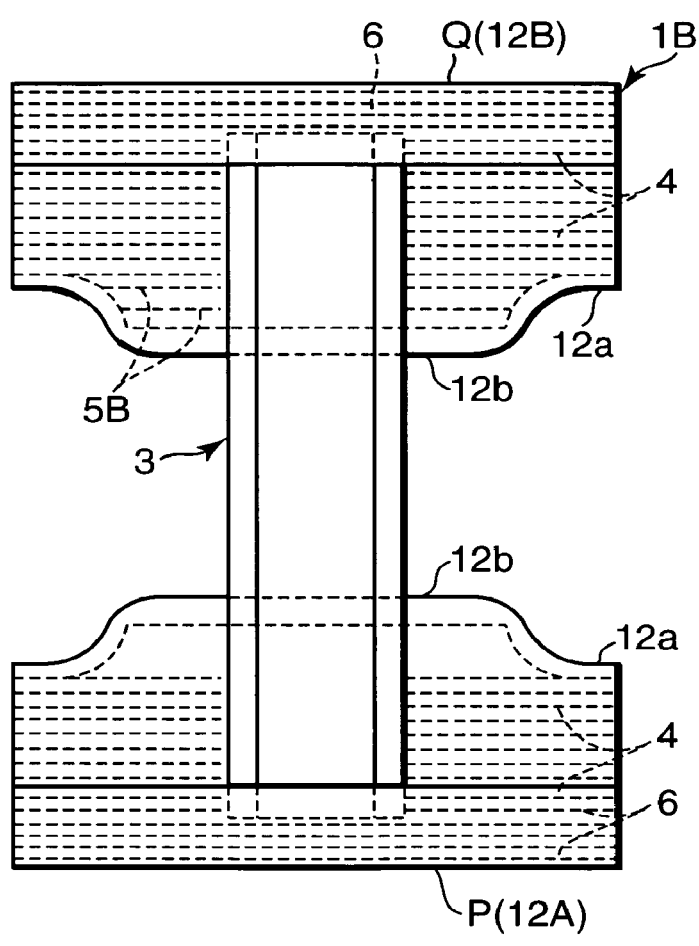
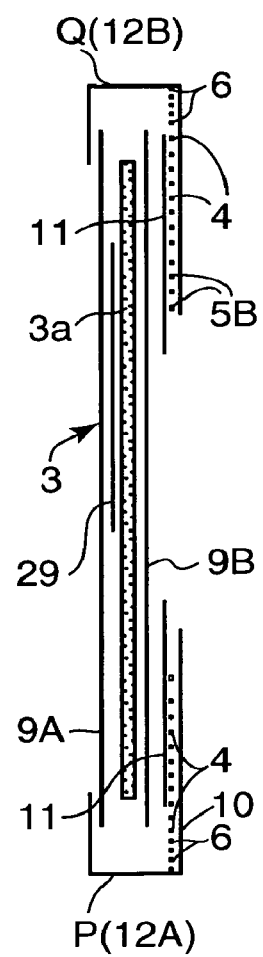

FIG.19A
FIG.19B
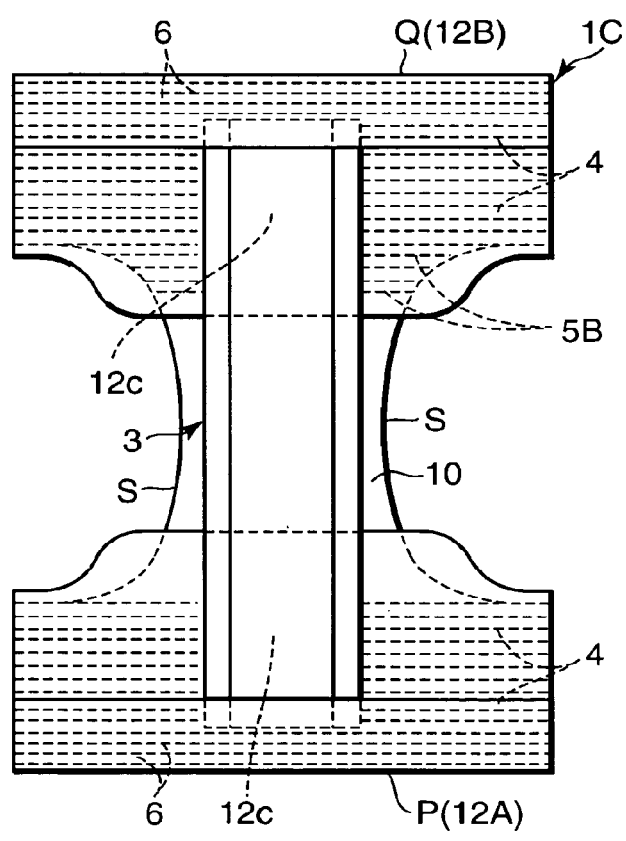
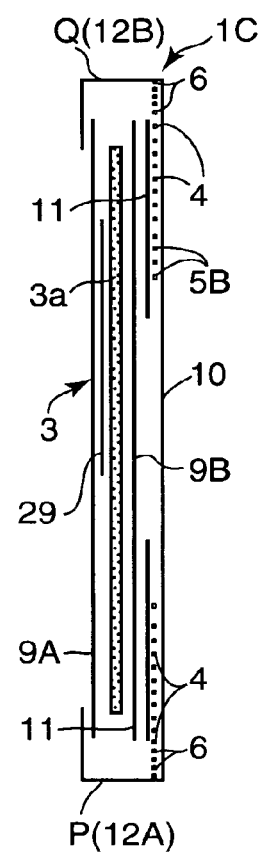

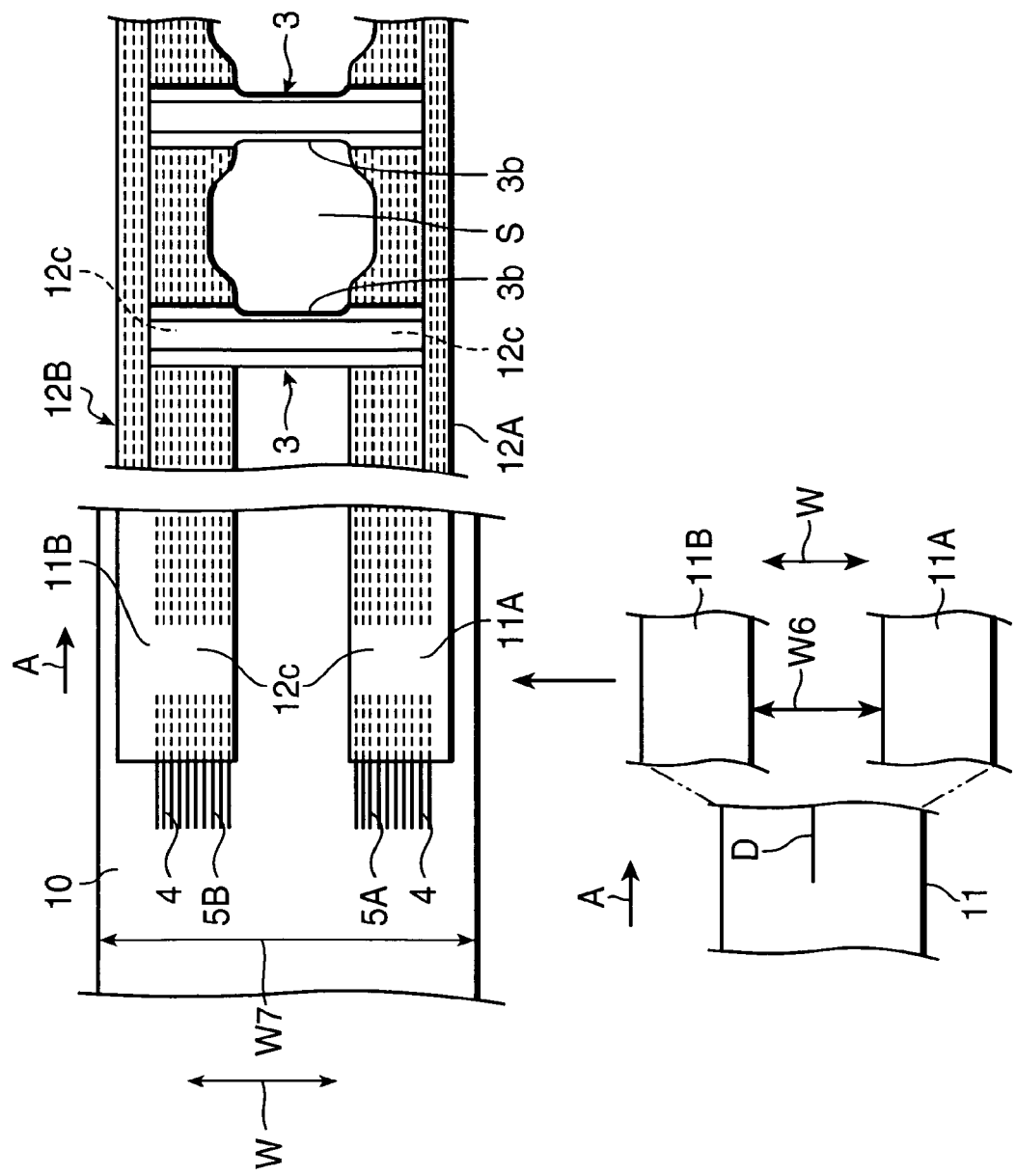

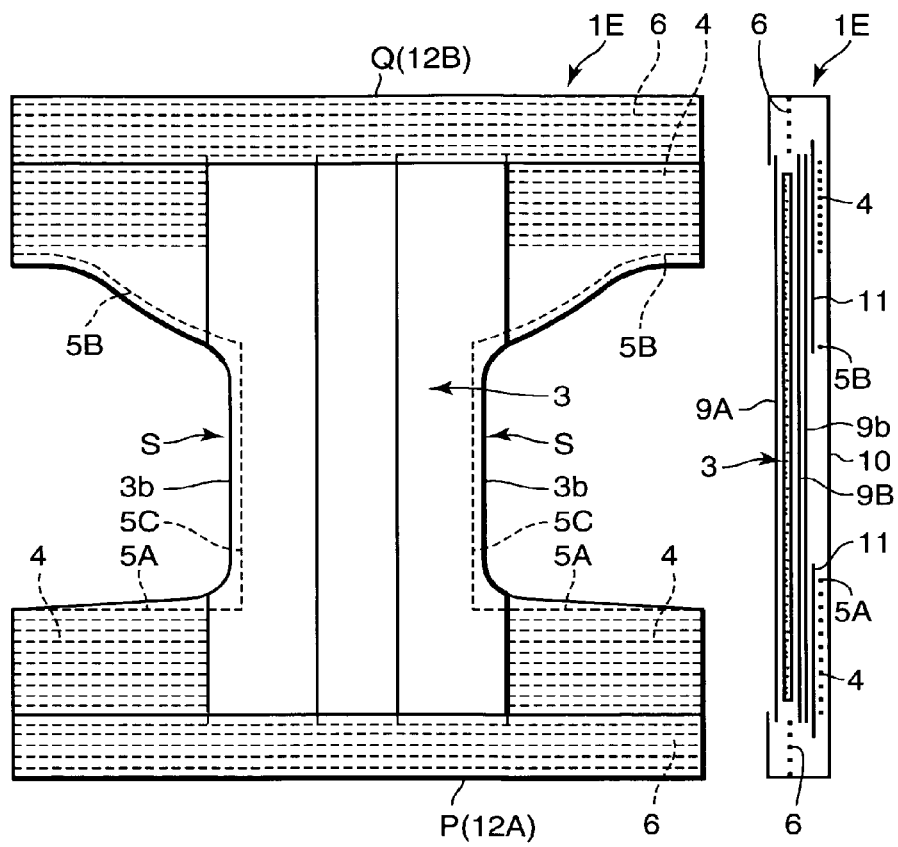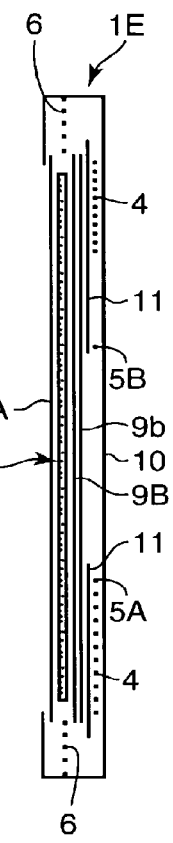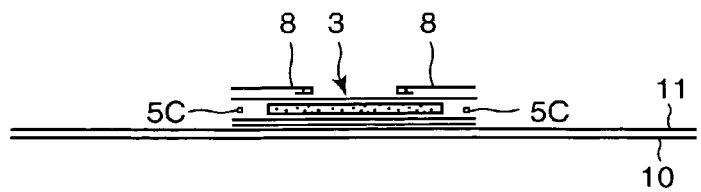

DISPOSABLE WEARING ARTICLE

CROSS-REFERENCE TO RELATED APPLICATIONS

This application is a divisional of U.S. patent application Ser. No. 10/565,151 filed on Jan. 19, 2006.

BACKGROUND OF THE INVENTION

1. Field of the Invention

The present invention relates to a method of continuously manufacturing disposable wearing articles, such as disposable diapers.

2. Description of the Related Art

As is shown in FIG. 28, in the step of manufacturing disposable wearing articles in a transverse flow state (see an arrow indicted by a capital A), it is known to cut a web 41 in the length direction so that concave portions 41a and convex portions 41b appear alternately, then widen a first web 41A and a second web 41B, and attach absorbers 42 to bridge between the concave portions 41a and the convex portions 41b of the first web 41A and the second web 41B (see Japanese Unexamined Patent Publication Nos. 2002-306534 and 002-272781).

When the web 41 is cut into the first web 41A and the second web 41B, however, tension in the length direction of the web is kept applied on portions including W11, whereas tension is no longer applied on portions including W12 because these portions are in open width and therefore hard to hold. This readily gives rise to wrinkles in the portions including W12 (convex portions 41b), and a problem arises when absorbers are attached. In a case where an elastic member is inserted in the web 41 in the length direction of the web, a contractive force in the length direction is induced in the portions including W12 (convex portions 41b) after the web is cut, which gives rise to wrinkles and creases. In particular, in a case where a leg peripheral elastic member 43 is inserted in the portions (convex portions 41b) including W12 along convex portions, a contractive force is induced in a direction different from the direction of the tension that is applied while the web is transported in open width. This gives rise to more significant wrinkles and creases, and a problem arises when the absorbers are attached.

SUMMARY OF THE INVENTION

It is an object of the invention to provide a manufacturing method of a disposable wearing article that is free from the problems residing in the prior art.

It is another object to provide a manufacturing method of a disposable wearing article that does not raise a problem attributed to the occurrence of wrinkles when the absorber is attached by reducing the occurrences of wrinkles and creases when the web is cut.

According to an aspect of the invention, a web is cut in a length direction so that a concave portion and a convex portion appear alternately. A cover sheet or an absorber is attached to the cut first web and second web after or before widening the first web and the second web.

These and other objects, features, aspects, and advantages of the present invention will become more apparent from the following detailed description of the preferred embodiments/examples with reference to the accompanying drawings.

BRIEF DESCRIPTION OF THE DRAWINGS

FIG. 10 shows a disposable wearing article of a first modification, FIG. 10A being a plan view in a developed state and FIG. 10B being a sectional side elevation;

FIG. 16 is a plan view showing a manufacturing status in major steps;

FIG. 17 is a disposable wearing article of the second embodiment, FIG. 17A being a plan view in a developed state and FIG. 17B being a schematic sectional side elevation;

FIG. 19 shows a disposable wearing article of the third embodiment, FIG. 19A being a plan view in a developed state and FIG. 19B being a schematic sectional side elevation;

FIG. 26 is a plan view showing a manufacturing status in major steps;

FIG. 27 shows a disposable wearing article of the fifth embodiment, FIG. 27A being a plan view in a developed state, FIG. 27B being a schematic sectional side elevation, and FIG. 27C being a schematic sectional bottom view.

DETAILED DESCRIPTION OF THE PREFERRED EMBODIMENTS

Hereinafter, best modes for carrying out the invention will be described in detail with reference to the drawings.

First Embodiment

FIG. 1 through FIG. 14 show a disposable wearing article 1A of a first embodiment and a manufacturing method of the same.

Figure 9A:
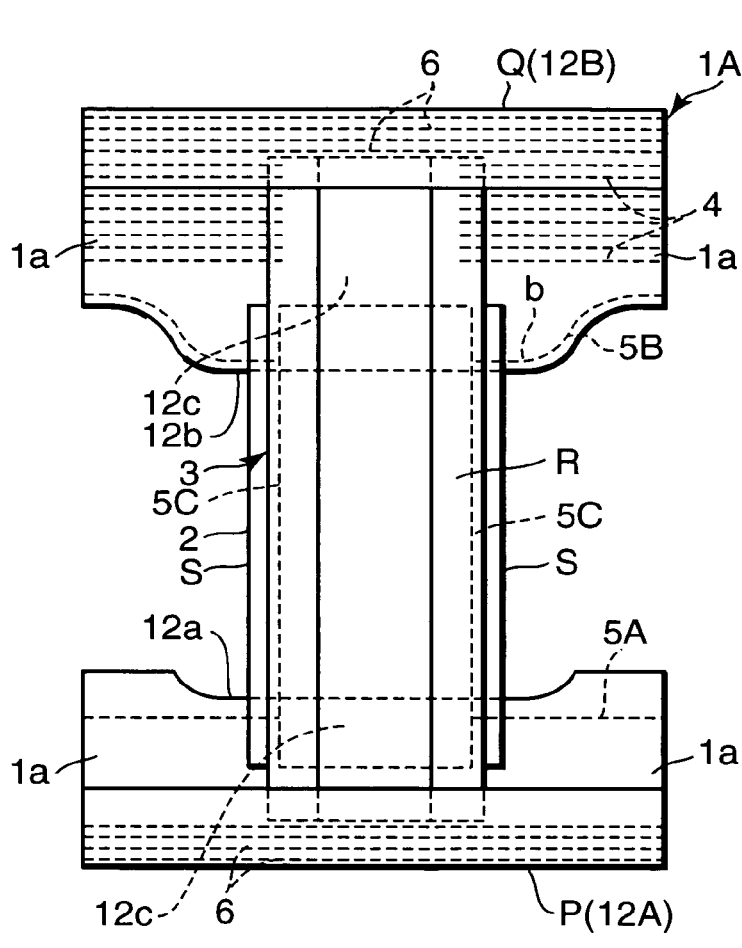
FIG. 9 shows a disposable wearing article of the first embodiment, FIG. 9A being a plan view in a developed state, FIG. 9B being a schematic sectional side elevation, and FIG. 9C being a schematic sectional bottom view.
Figure 9B:
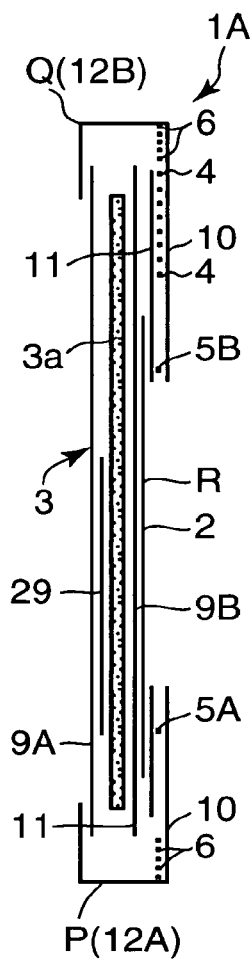
Figure 9C:
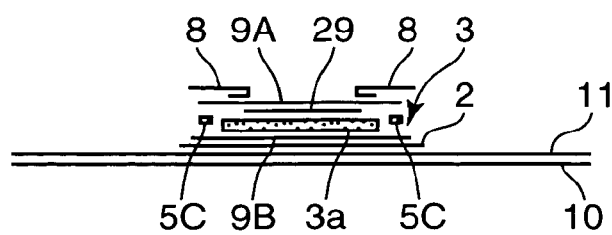
Figure 12:
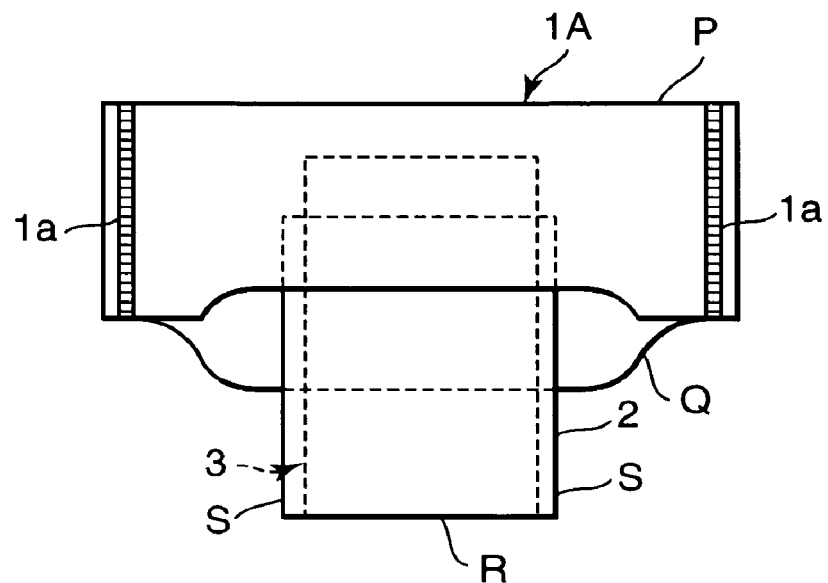
FIG. 12 is a front view of the disposable wearing article of the first embodiment in a fabricated state.

FIG. 9 shows a state where the disposable wearing article 1A is developed. FIG. 9A is a plan view, FIG. 9B is a schematic sectional side elevation, and FIG. 9C is a schematic sectional bottom view. FIG. 12 is a front view of the disposable wearing article 1A in a fabricated state.

As is shown in FIG. 9, the disposable wearing article 1A includes a cover sheet 2 attached to bridge between a front portion (first elastic laminated body 12A) P and a back portion (second elastic laminated body 12B) Q, and an absorber 3 is attached onto the cover sheet 2. The front portion P and the back portion Q are placed one on the other by folding the absorber 3 inward with the cover sheet 2 on the outside, and an article of an underpants type as is shown in FIG. 12 is fabricated by side-sealing the both side portions 1a of the front portion P and the back portion Q. The both side portions 1a may not be side-sealed, and instead, the both side portions 1a may be stopped in an attachable/detachable manner using a stopper tape or the like, so that an article of a tape type is obtained.

In the disposable wearing article 1A, a crotch portion R is defined by the absorber 3 and leg opening portions S are formed on the both sides of the absorber 3.

The manufacturing method of the disposable wearing article 1A of the first embodiment will now be described with reference to FIG. 1 through FIG. 8.

(1) Steps 1 through 5 show a step of manufacturing the first elastic laminated body 12A on the front portion P side and the second elastic laminated body 12B on the back portion Q side from an elastic laminated body 12 in a transverse flow state, and then attaching the cover sheet 2.

Figure 1:
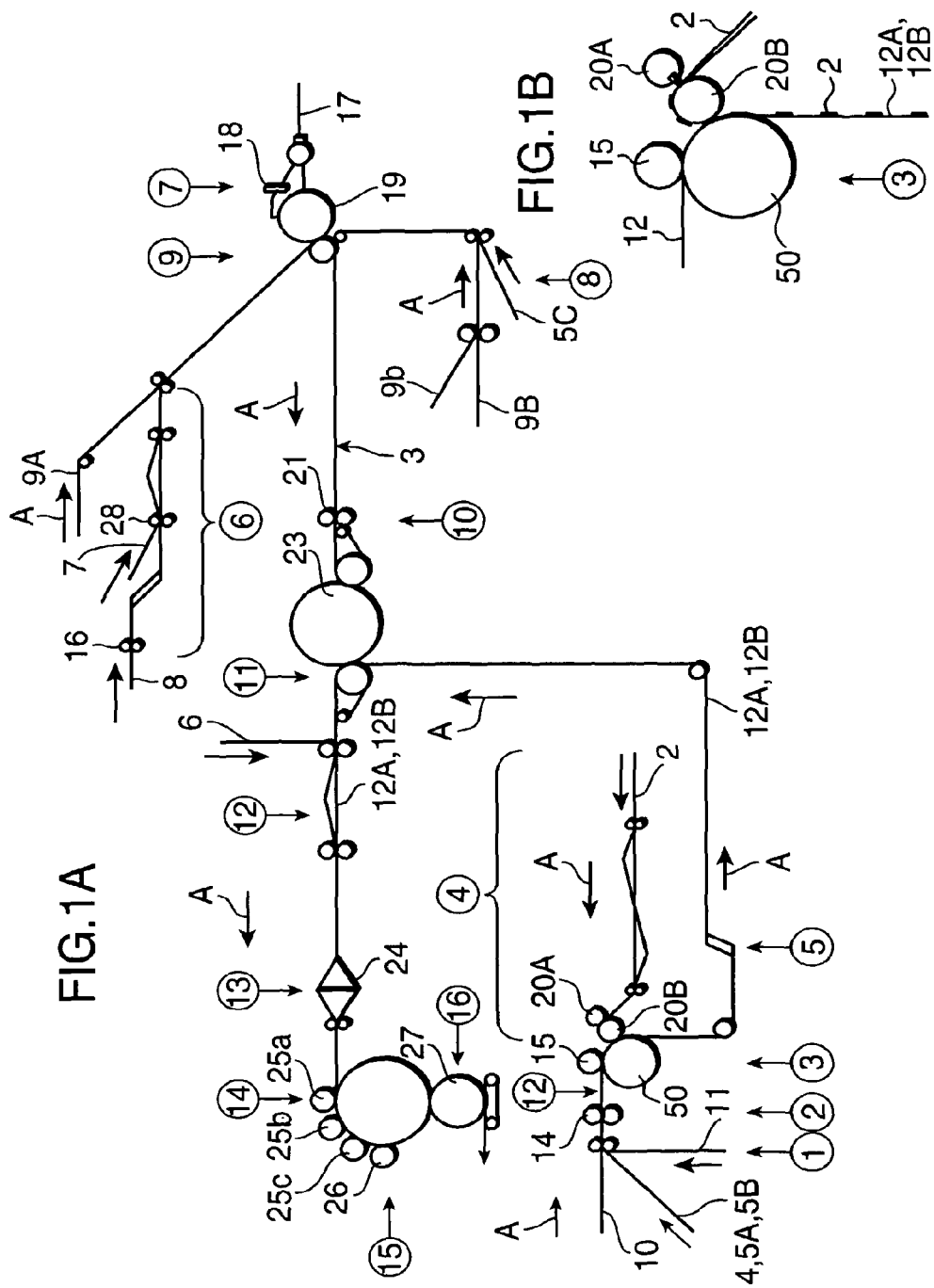
FIG. 1 is a system view detailing the manufacturing steps of a disposable wearing article of a first embodiment, FIG. 1A being a general view and FIG. 1B being an enlarged view of a major portion.
Figure 2:
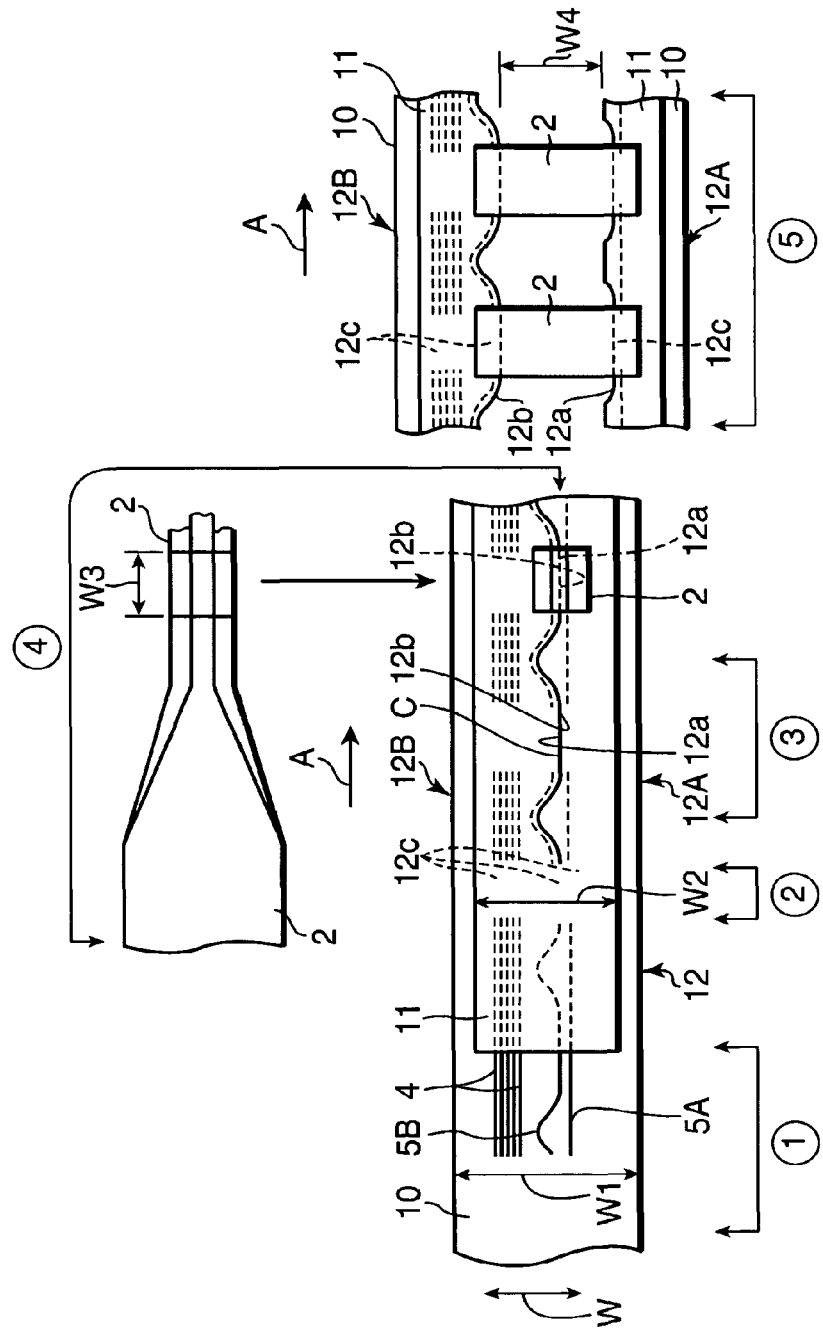
FIG. 2 is a plan view showing a manufacturing status in Steps 1 through 5.
Figure 6A:
FIGS. 6A through 6F are cross sections of major portions showing the manufacturing status in Steps 1 through 5.
Figure 6B:
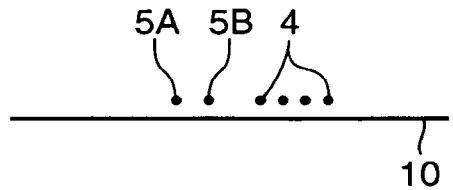
Figure 6C:
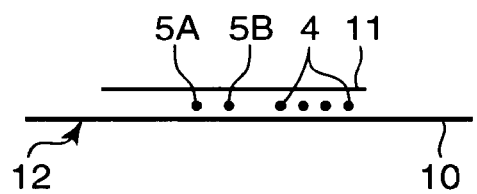

[Step 1] Referring to FIG. 1, FIG. 2, and FIG. 6, the elastic laminated body 12 is manufactured by bonding an outer surface web 10 and an inner surface web 11 that are made of non-woven fabric and fed continuously in a length direction A while inserting body-fitting elastic members 4 and leg peripheral elastic members 5A and 5B on the front portion P side and the back portion Q side in an extended state in the length direction A in between (see FIGS. 6A through 6C). By taking displacement in width at the time of bonding into account, it is preferable to set a breadth W2 of the inner surface web 11 narrower than a breadth W1 of the outer surface web 10.

The leg peripheral elastic member 5A and the body-fitting elastic member 4 are attached linearly in the length direction A, whereas the leg peripheral elastic member 5B is attached in a curved line to go along the concave portion 12b that will be described below.

For example, a hot melt adhesive is applied on at least one of the webs 10 and 11, so that these webs 10 and 11 are bonded to each other while the body-fitting elastic member 4 and the leg peripheral elastic members 5A and 5B are inserted in between.

Polyurethane, natural rubber, heat curable resin, etc. can be used as materials of the body-fitting elastic member 4 and the leg peripheral elastic members 5A and 5B. These members can be of a thread shape or a ribbon shape. Also, the number of each member is not limited to one, and each member may be made of more than one thread or ribbon. In a case where heat curable resin is used as the material, when the heat curable resin itself has a capability of bonding the webs 10 and 11, the hot melt adhesive may be omitted. It should be noted that the same description applies to materials and shapes of elastic members 5C, 6, and 7 described below.

[Step 2] The elastic laminated body 12 is cut into the first elastic laminated body 12A and the second elastic laminated body 12B in the length direction A so that concave portions 12a and convex portions (leg peripheral flap portions) 12b appear alternately in Step 3 described in the following. In preceding Step 2, portions 12c where contractive forces are lessened are formed by applying treatment to lessen contractive forces of the body-fitting elastic members 4 and the leg peripheral elastic members 5A and 5B in the concave portions 12a and the convex portions 12b on the second elastic laminated body 12B side.

As the treatment to lessen contractive forces, for example, a method of fusing the body-fitting elastic member 4 and the leg peripheral elastic members 5A and 5B using an embossed roll (heat embossing) (see JP-A-2002-113042), or a method of cutting the body-fitting elastic member 4 and the leg peripheral elastic members 5A and 5B using a gather cutter 14 (see FIG. 1) can be adopted. It is preferable to fuse or cut these members while the elastic laminated body 12 placed along the roll is drawn in vacuum. The step of lessening contractive forces can be performed at any timing before Step 11 of attaching the absorber 3 described below.

Figure 6D:
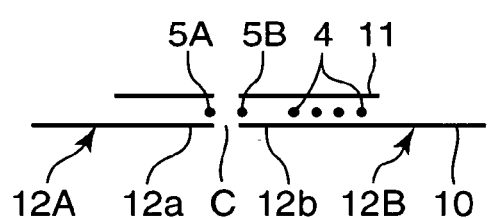
Figure 6E:
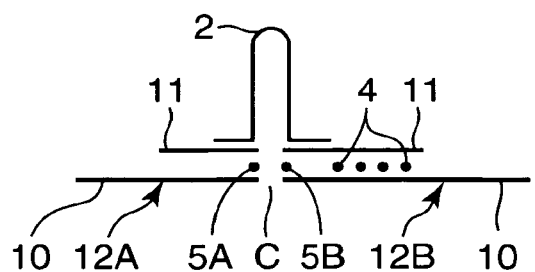

[Step 3] The first elastic laminated body 12A and the second elastic laminated body 12B are manufactured by cutting the elastic laminated body 12 in the length direction A using an S-cutter 15 (so-called S-cutting, see a cutting line C), so that the concave portions 12a and the convex portions 12b appear alternately in the elastic laminated body 12 (see FIG. 6D). The cutting may be made in the form of a perforated line so that laminated bodies can be separated at the time of widening described below.

Figure 13:
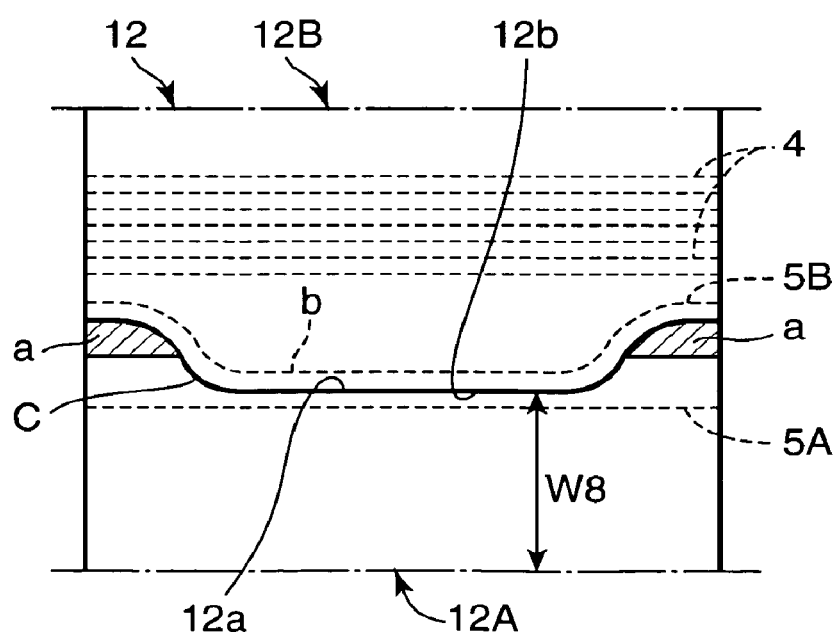
FIG. 13 is a plan view showing an attachment state of an elastic member in an elastic laminated body and a cutting line.

As is shown in FIG. 13, when the elastic laminated body 12 is cut into the first elastic laminated body 12A and the second elastic laminated body 12B by the S-cutting (see the cutting line C), circular arc portions indicated by hatching a are left on the both sides of the first elastic laminated body 12A. These circular arc portions may be left intact or may be cut off from the design consideration. FIG. 9 through FIG. 12 show the disposable wearing article 1A of an underpants type with these portions being cut off.

A length W8 of the elastic laminated body 12A in the width direction may be extended. In such a case, the raise length can be extended, which can in turn increase the commercial value.

[Step 4] The liquid-impermeable cover sheet 2 continuously fed in the length direction A is folded in the shape of Ω by providing slack comparable to the widening described below, and then cut in a specific width W3 (see FIG. 2) using cut and place rollers 20 (A and B). The cover sheet 2 thus cut is bonded to bridge between the inner surface webs 11 on the concave portion 12a and the convex portion 12b of the first elastic laminated body 12A and the second elastic laminated body 12B, respectively (see FIG. 6E).

It is preferable to bond the cover sheet 2 to the inner surface webs 11 when wrinkles are hardly produced in the convex portion 12*b* of the second elastic laminated body 12B, and it is particularly preferable to perform bonding immediately after the cutting in Step 3.

As is shown in FIG. 1B, it is preferable that the cover sheet 2 folded in the shape of Ω is cut by the cut roller 20A, then transported on the place roller 20B, and bonded to bridge between the inner surface webs 11 on the concave portion 12*a* and the convex portion 12*b* of the first elastic laminated body 12A and the second elastic laminated body 12B, respectively, on a back sheet lamination drum 50.

The cover sheet 2 can be hydrophobic non-woven fabric, such as PP and PE.

For the cover sheet 2, the width W3 is set to be almost equal to that of the absorber 3 and the length is set shorter than that of the absorber 3. By taking into account displacement in width caused when the absorber 3 is attached, it is preferable in practice to set the width W3 of the cover sheet 2 about 6 to 13% wider.

Figure 6F:
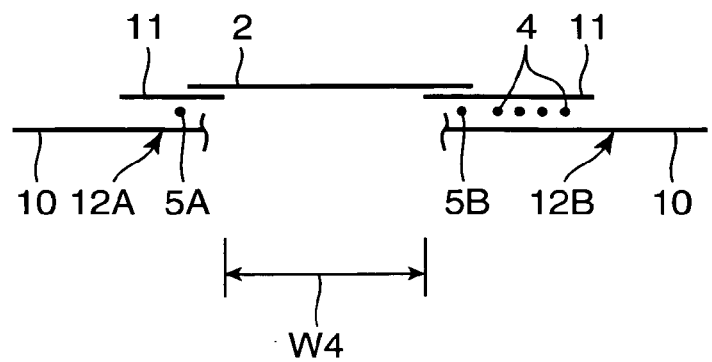

[Step 5] The cut first elastic laminated body 12A and second elastic laminated 12B are widened by a specific interval W4 in the width direction W (see FIG. 6F). The cover sheet 2 is thus expanded to be flat and bridge between the concave portions 12*a* and the convex portions 12*b* of the first elastic laminated body 12A and the second elastic laminated body 12B, respectively.

(2) Step 6 through Step 10 show one example of a step of manufacturing the absorber 3.

Figure 3:
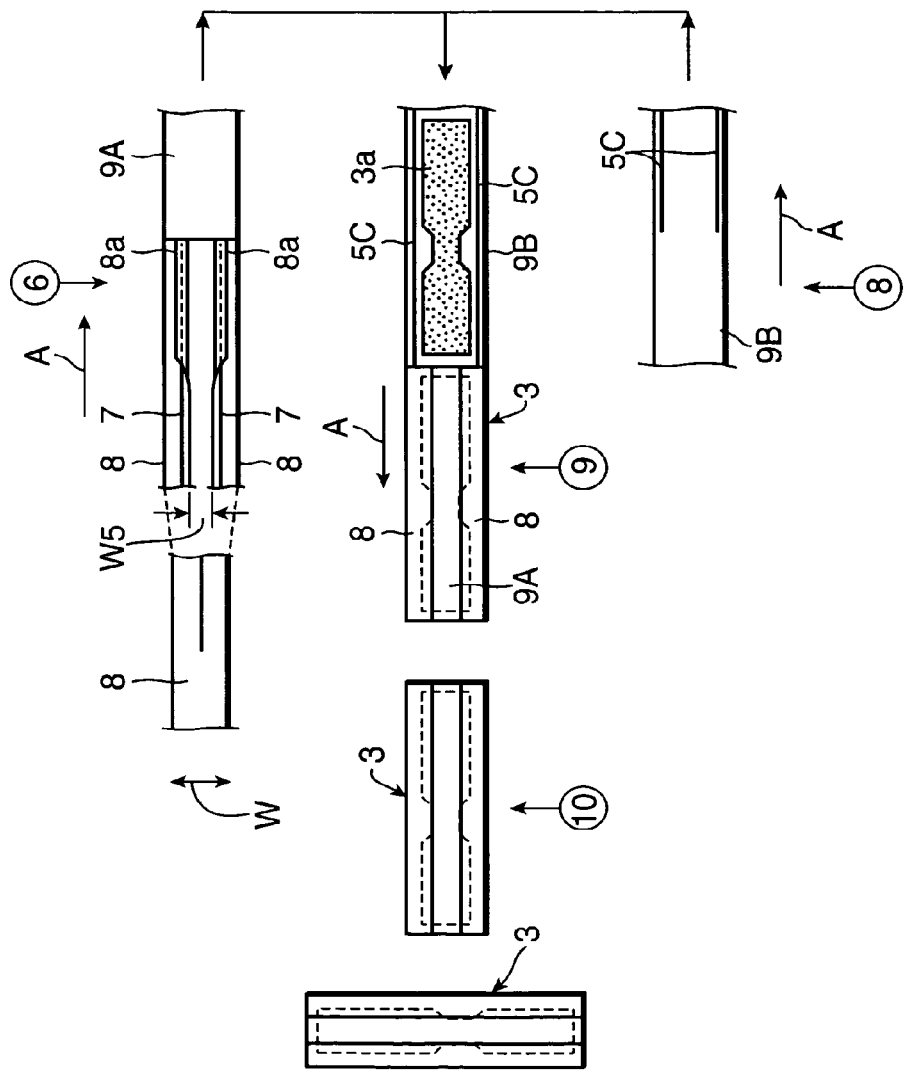
FIG. 3 is a plan view showing a manufacturing status in Steps 6 through 10.
Figure 7A:
FIGS. 7A through 7F are cross sections of major portions showing the manufacturing status in Steps 6 through 10.
Figure 7B:
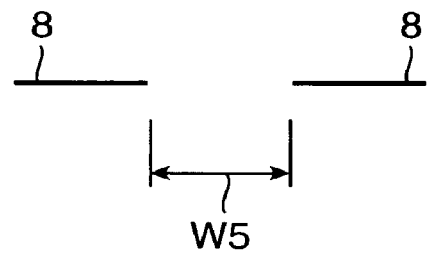
Figure 7C:
Figure 7D:
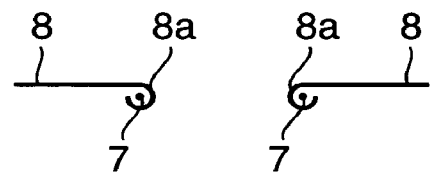
Figure 7E:
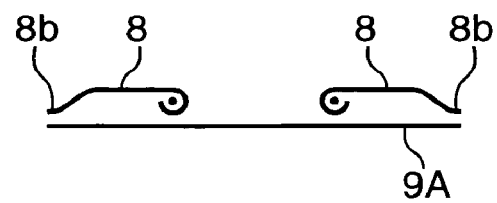

[Step 6] Referring to FIG. 1, FIG. 3, and FIG. 7, a sheet for rising flaps 8 that is made of non-woven fabric and fed continuously in the length direction A is cut in the length direction A by a slitter 16 (see FIG. 7A). The cut rising flaps 8 are widened by a specific interval W5 in the width direction W (see FIG. 7B). Subsequently, a flap elastic member 7 in an extended state in the length direction A is inserted and bonded to the interior of an incurved portion 8*a* of each rising flap 8 curled inwardly using a sailor 28 (see FIGS. 7C and 7D). Subsequently, rear anchor portions 8*b* of the rising flaps 8 are bonded to the both side portions of a top sheet 9A that is made of liquid-permeable non-woven fabric and fed continuously in the length direction A (see FIG. 7E).

[Step 7] A core 3*a* of the absorber 3 is molded in a longitudinal flow state by laminating fibrillated fluff made by pulverizing a roll pulp 17 using a pulverizer 18 on a pattern drum 19. The fluff may be mixed with super absorbent polymer.

[Step 8] Leg peripheral elastic members 5C in an extended state in the length direction A are attached along the both side portions of a back sheet 9B that is made of non-woven fabric and fed continuously in the length direction A while a liquid-impermeable synthetic resin film 9*b* is bonded to the back surface.

In this embodiment, because the cover sheet 2 can be used as the non-woven fabric back sheet, the back sheet 9B may be made of only a liquid-impermeable waterproof film, such as a polyethylene film, in this step. In such a case, the leg peripheral elastic members are also attached along the both side portions in the same manner.

Figure 7F:
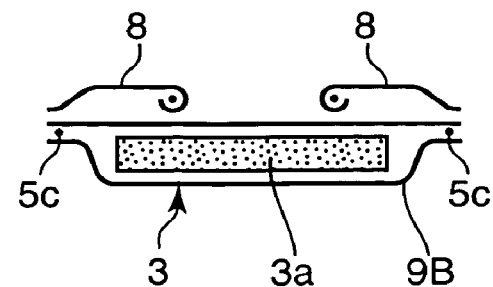

[Step 9] The absorber 3 in a lengthy state in the length direction A is manufactured by placing the core 3*a* on the back sheet 9B manufactured in Step 8, and bonding the top sheet 9A manufactured in Step 6 to the back sheet 9B with a hot melt adhesive or the like while the core 3*a* and the leg peripheral elastic members 5C are inserted in between (see FIG. 7F).

As the liquid-impermeable sheet, a polyethylene film or a water-shedding or breathable non-woven fabric is preferable.

As the liquid-permeable sheet, a liquid-permeable non-woven fabric or a mesh sheet is preferable.

[Step 10] The absorber 3 of a rectangular shape is manufactured by cutting the absorber 3 in a lengthy state in the length direction A together with the rising flaps 8 at every specific length using an interior cutter 21.

A transfer sheet 29 (see FIG. 9) may be interposed between the core 3*a* and the top sheet 9A. The transfer sheet 29 diffuses urine or the like quickly and prevents leakage of absorbed urine or the like from the top sheet 9A.

In a case where the core 3*a* is molded by mixing the super absorbent polymer with the fluff, it is possible to prevent the super absorbent polymer from coming out from the fluff by sandwiching the core 3*a* between two sheets of tissue paper or wrapping the core 3*a* in a single sheet of tissue paper.

(3) Step 11 through Step 16 show a step of fabricating the disposable wearing article 1A in a transverse flow state.

Figure 4:
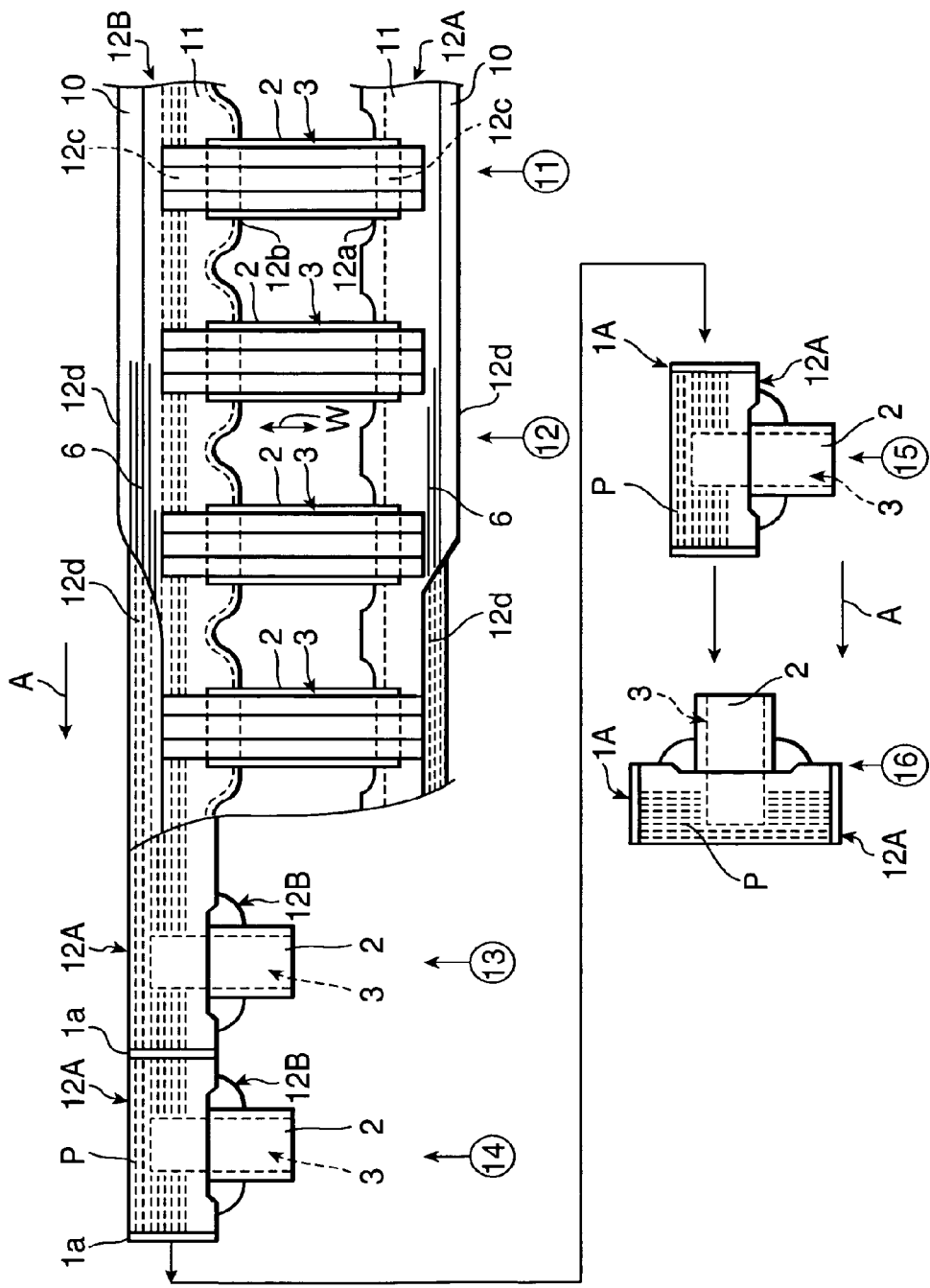
FIG. 4 is a plan view showing a manufacturing status in Steps 11 through 16.
Figure 5:
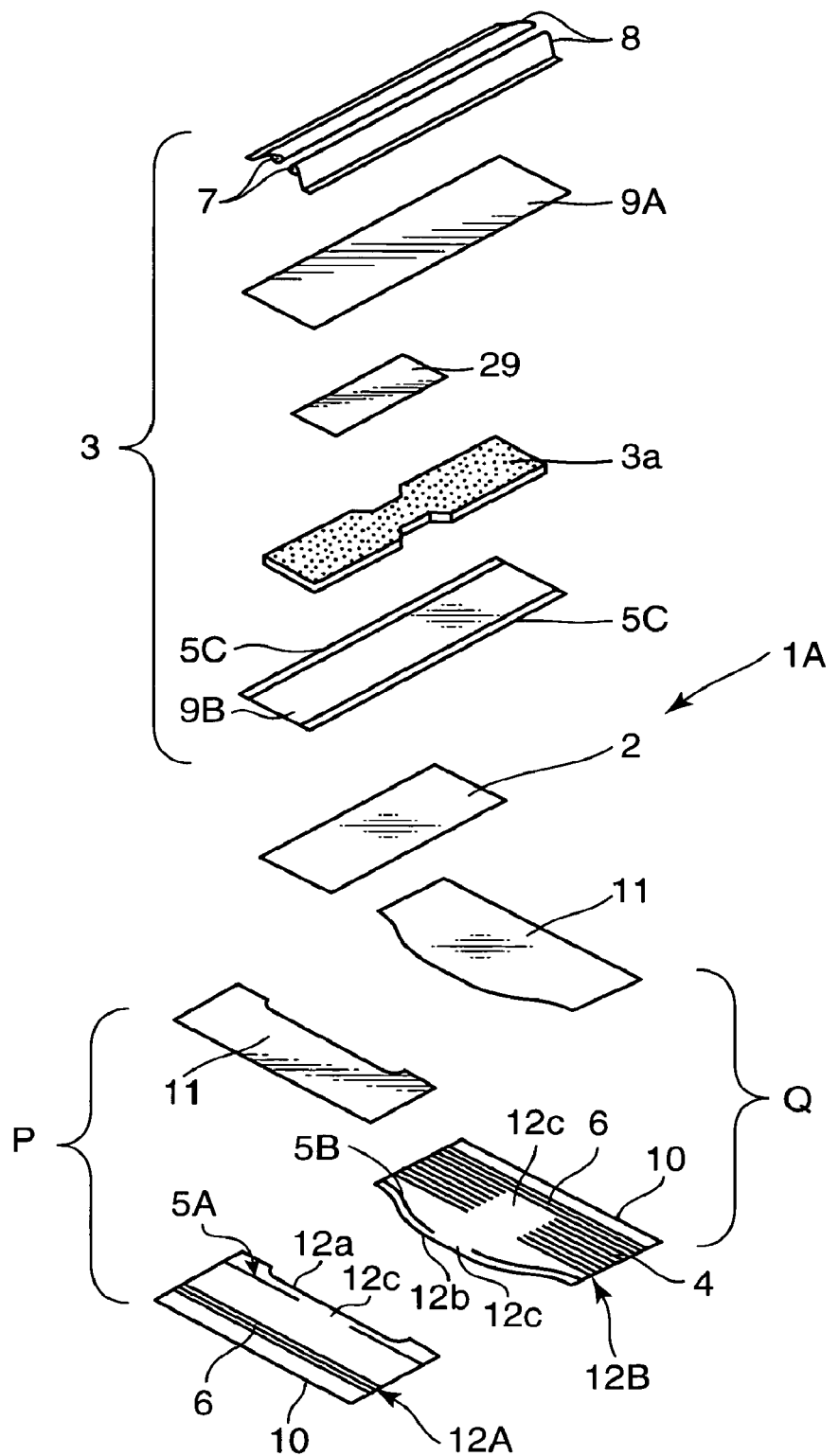
FIG. 5 is an exploded perspective view of a disposable wearing article.
Figure 8A:
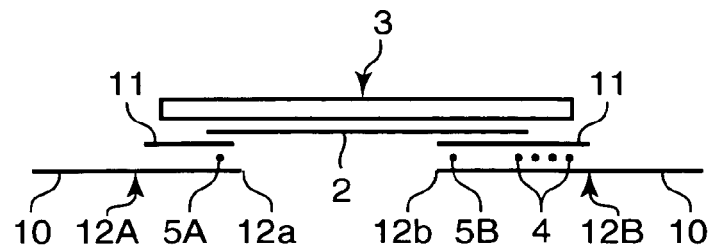
FIGS. 8A through 8D are cross sections of major portions showing the manufacturing status in Steps 11 through 16.
Figure 8B:
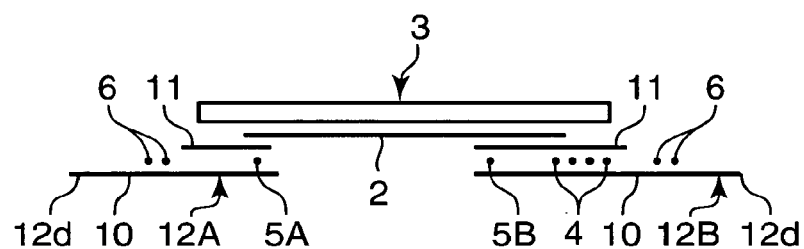
Figure 8C:
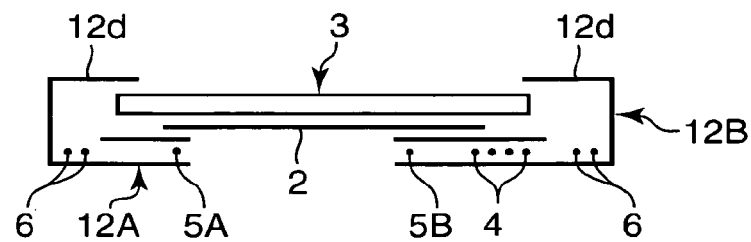

[Step 11] Referring to FIG. 1, FIG. 4, and FIG. 8, as with the first elastic laminated body 12A and the second elastic laminated body 12B in a transverse flow state manufactured in Step 5, the absorber 3 manufactured in Step 10 is brought into a transverse flow state by being inverted by 90 degrees using an interior turn drum 23 (see the left end of FIG. 3), and the absorber 3 is bonded onto the cover sheet 2 bonded to bridge between the first elastic laminated body 12A and the second elastic laminated body 12B, and is also bonded to bridge between the inner surface webs 11 on the concave portion 12*a* and the convex portion 12*b* of the first elastic laminated body 12A and the second elastic laminated body 12B, respectively (see FIG. 8A). In this case, the absorber 3 is bonded across the portion 12*c* where contractive forces of the concave portion 12*a* and the convex portion 12*b* are lessened.

[Step 12] Waist elastic members 6 in an extended state in the length direction A are placed along the both end portions 12*d* of the first elastic laminated body 12A and the second elastic laminated body 12B in the width direction (a direction crossing with the length direction A) W on the outer surface web 10 side. The both end portions 12*d* are folded inward, so that the absorber 3 is bonded to the inner side of the both end portions 12*d* while the waist elastic members 6 are inserted in between (see FIGS. 8B and 8C). In order to prevent the fluff or the like from coming out from the end portions of the absorber 3 and/or leakage of absorbed urine or the like, it is preferable to bond the both end portions 12*d* to cover the top and bottom end portions of the absorber 3.

Subsequently, the leg hole portions S as described below may be formed by cutting out the first elastic laminated body 12A and the second elastic laminated body 12B using a trim cutter (not shown). Further, the both edge portions of the cover sheet may be cut off or the both edge portions of the absorber 3 may be cut off.

Figure 8D:
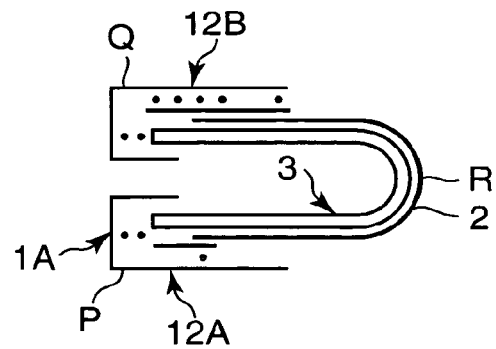

[Step 13] The first elastic laminated body 12A and the second elastic laminated body 12B are placed one on the other by folding the absorber 3 inward with the cover sheet 2 on the outside using a doubling device 24 (see FIG. 8D).

[Step 14] The intermediate position (equivalent to the both side portions 1*a* of the disposable wearing article 1A) of the absorber 3 adjacent to the first elastic laminated body 12A and the second elastic laminated body 12B placed one on the other is side-sealed by fusing heat seals 25*a* through 25*c* in several steps. The heat seals 25*a* through 25*c* are not necessarily in the several steps. Instead of using the heat seals 25*a* through 25*c*, the side-sealing may be performed using sonic.

[Step 15] The disposable wearing article 1A with the both side portions 1*a* being side-sealed can be achieved by cutting the intermediate portion in the side-sealed portions of the first elastic laminated body 12A and the second elastic laminated body 12B using a product cutter 26.

[Step 16] The disposable wearing article 1A as the product is inverted by 90 degrees by a product inverting device 27, and transported to a product inspection step and to a packing step.

According to the manufacturing method of the disposable wearing article 1A of the first embodiment, the elastic laminated body 12 is manufactured by bonding the two webs 10 and 11 while inserting the elastic members 4, 5A, and 5B in between. The elastic laminated body 12 is then cut in the length direction A so that the concave portions 12a and the convex portions 12b appear alternately. After the cover sheet 2 is bonded to bridge between the concave portion 12a and the convex portion 12b of the cut first elastic laminated body 12A and second elastic laminated body 12B, respectively, the first elastic laminated body 12A and the second elastic laminated body 12B are widened. The absorber 3 is then attached onto the cover sheet 2.

The cover sheet 2 is therefore bonded to bridge between the first elastic laminated body 12A and the second elastic laminated body 12B not after the widening when wrinkles are readily produced in the elastic laminated body 12, but before the widening when wrinkles are hardly produced, more specifically, immediately after the cutting. It is thus possible to avoid a problem attributed to wrinkles and arising when the absorber 3 is attached.

Also, the method of the invention is particularly effective in a case where the wrinkles and/or creases are more readily produced as described above, for example, in a case where the leg peripheral elastic member 5B is inserted in the convex portion 12b.

In addition, the bonding can be readily performed by bonding the cover sheet 2 provided with slack comparable to the widening to bridge between the first elastic laminated body 12A and the second elastic laminated body 12B. A stretchable sheet may be used as the cover sheet 2. In such a case, a stretchable absorber 3 can be used, which can in turn improve the feeling of fitness of the wearer.

Further, by setting the width W3 of the cover sheet 2 to be almost equal to that of the absorber 3 and by setting the length shorter than that of the absorber 3, the material costs can be saved in comparison with a manufacturing method of manufacturing the cover sheet 2 integrally with the absorber 3. By taking into account displacement in width caused when the absorber is attached, it is preferable in practice to set the width W3 of the cover sheet 2 about 6 to 13% wider.

Also, by making the cutting in the elastic laminated body 12 in the form of a perforated line so that the laminated bodies can be separated at the time of widening, it is possible to forestall a problem that wrinkles are readily produced at the same time instant the cutting is performed.

Furthermore, by attaching the waist elastic members 6, the body-fitting elastic member 4, and the leg peripheral elastic member 5A and 5B to the first elastic laminated body 12A and the second elastic laminated body 12B, it is possible to prevent the disposable wearing article 1A put on the wearer from drooping down by the waist elastic member 6, while the disposable wearing article 1A can be fit to the body by the body-fitting elastic members 4 and the adhesion to the leg portions can be enhanced by the leg peripheral elastic members 5A and 5B.

Also, by side-sealing the both side portions 1a of the first elastic laminated body 12A and the second elastic laminated body 12B while the absorber 3 is in a folded state, it is possible to achieve a wearing article of an underpants type.

In the first embodiment, the cover sheet 2 is bonded to bridge between the first elastic laminated body 12A and the second elastic laminated body 12B obtained by cutting the elastic laminated body 12 manufactured by bonding the two webs 10 and 11 while inserting the elastic members 4, 5A, and 5B in between. However, the cover sheet 2 may be bonded to bridge between a first web and a second web obtained by cutting a single web 11. It should be noted that the waist elastic member 6 that has no influence on the occurrence of wrinkles can be attached.

In such a case, because the cover sheet 2 is bonded to bridge between the first web and the second web not after the widening when wrinkles are readily produced, but before the widening when wrinkles are hardly produced, more specifically, immediately after the cutting, it is possible to avoid a problem attributed to wrinkles and arising when the absorber 3 is attached.

Figure 14A:
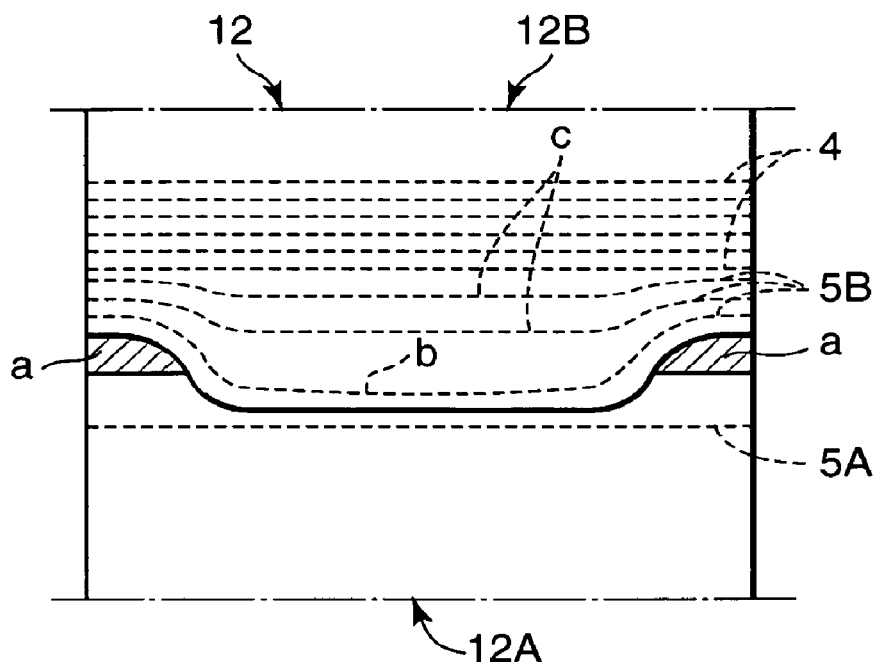
FIG. 14A is a plan view showing an attachment state of an elastic member in an elastic laminated body of a first modification and a cutting line.

In the disposable wearing article 1A of the first embodiment, as are shown in FIG. 9A and FIG. 13, the leg peripheral elastic member 5B on the second elastic laminated body 12B (back portion Q) side is attached in a curved line state b in the width direction of the wearing article. However, as are shown in FIG. 10 and FIG. 14A, the leg peripheral elastic member 5B can be attached to include both the curved line state b and a linear state c in the width direction of the wearing article.

Figure 11A:
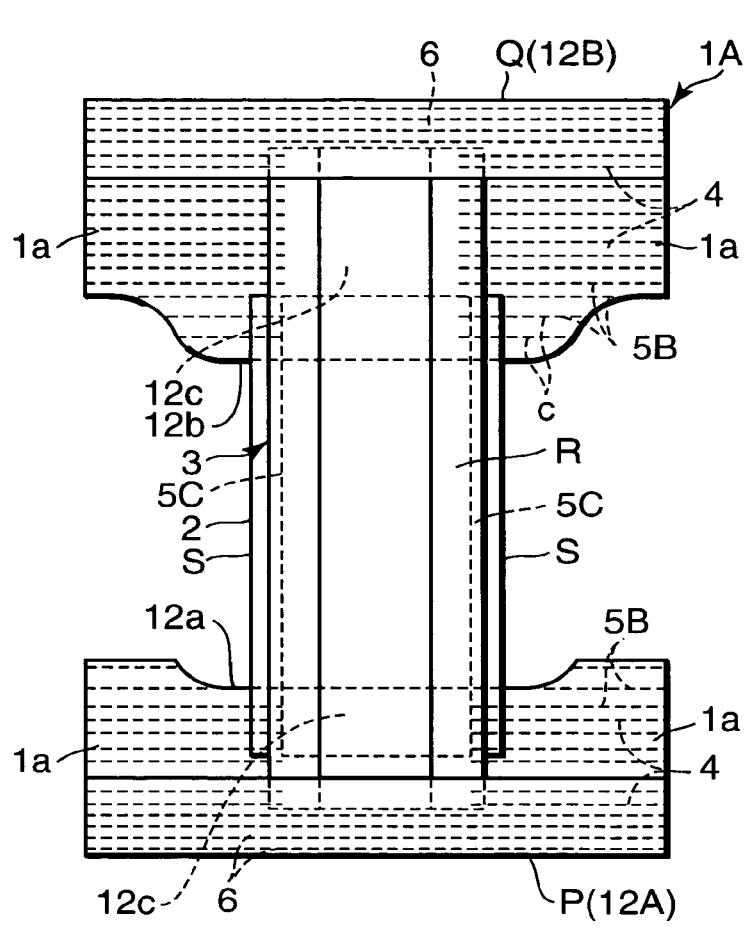
FIG. 11 shows a disposable wearing article of a second modification, FIG. 11A being a plan view in a developed state and FIG. 11B being a schematic sectional side elevation.
Figure 11B:
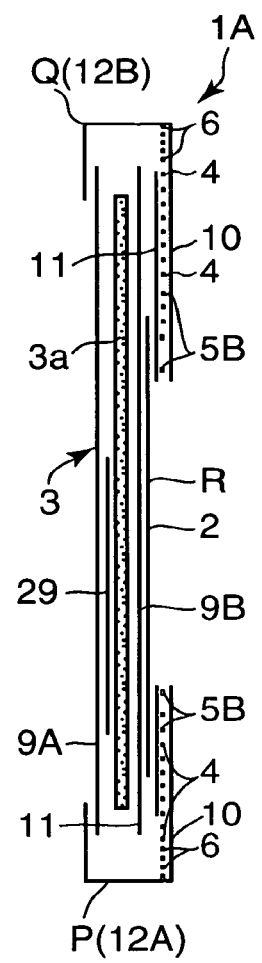
Figure 14B:
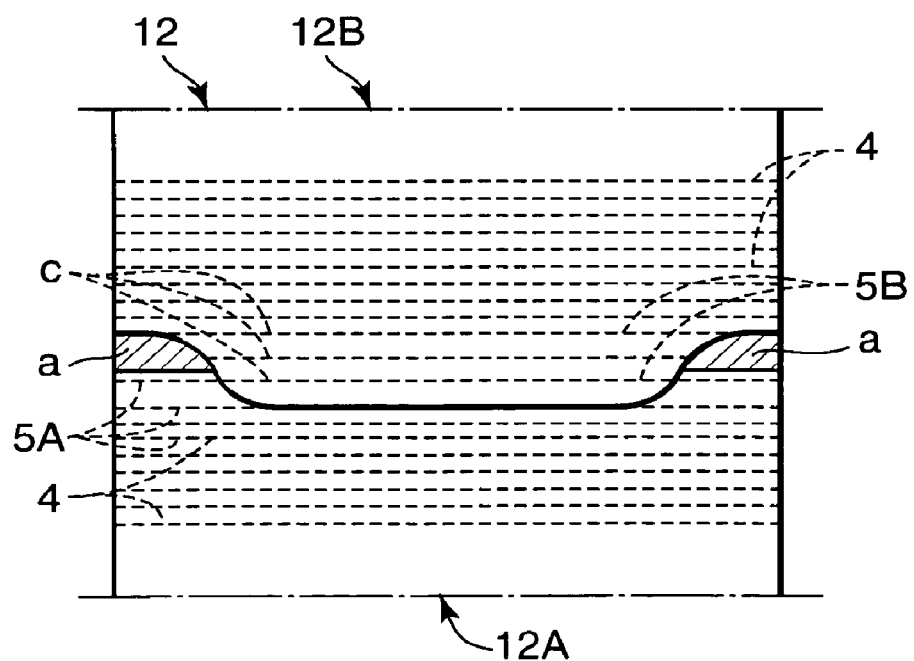
FIG. 14B is a plan view showing an attachment state of an elastic member in an elastic laminated body of a second modification and a cutting line.

Also, as are shown in FIG. 11 and FIG. 14B, the leg peripheral elastic member 5B can be attached in the linear state c in the width direction of the wearing article. The body-fitting elastic member 4 may be attached to the first elastic laminated body 12A (front portion P).

Second Embodiment

Figure 15:
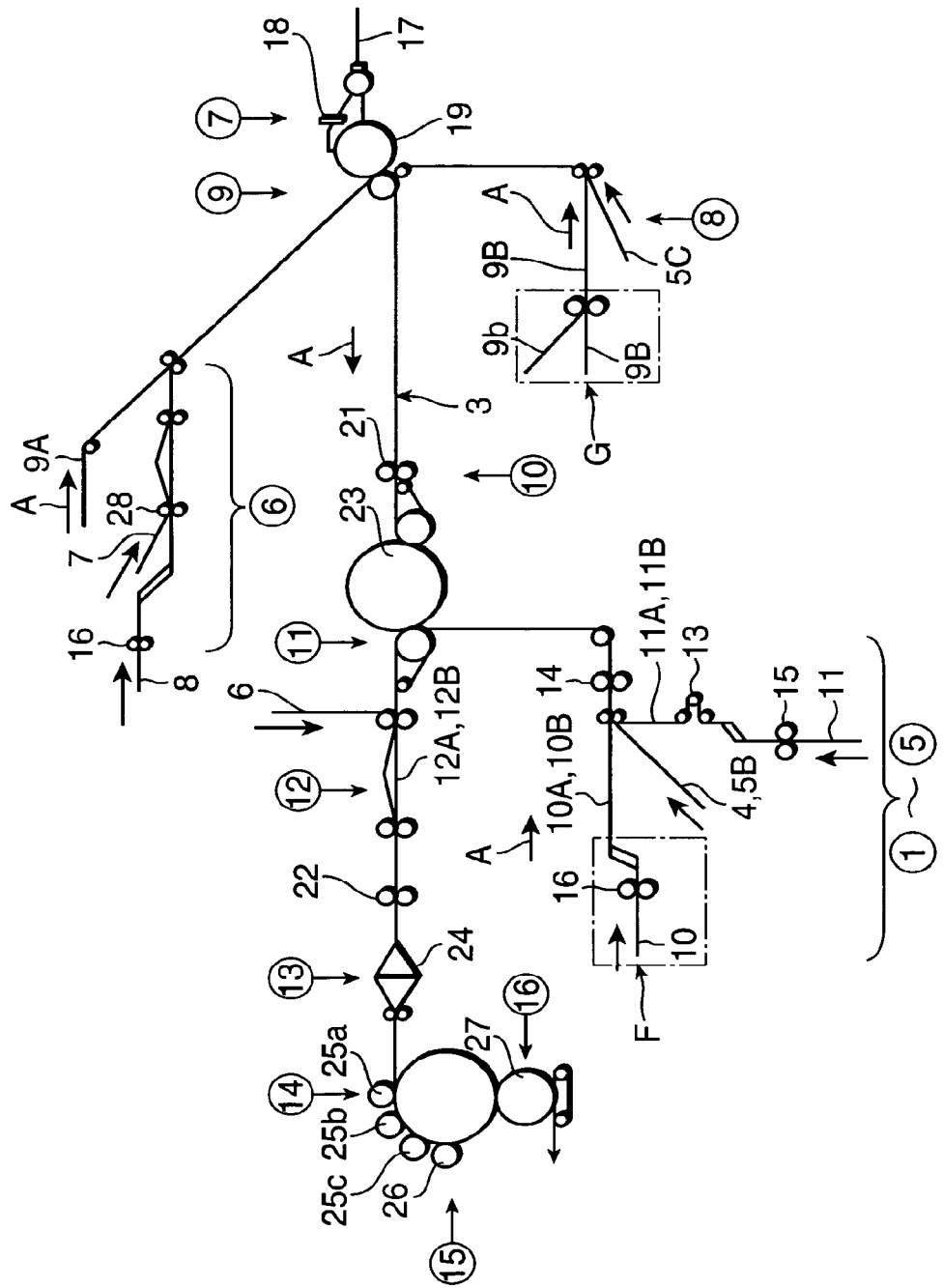
FIG. 15 is a system view detailing the manufacturing steps of a disposable wearing article of a second embodiment.

FIG. 15 through FIG. 17 show a manufacturing method of a disposable wearing article 1B of a second embodiment.

In comparison with the disposable wearing article 1A of the first embodiment, the disposable wearing article 1B of the second embodiment is different in that the cover sheet 2 is omitted.

The manufacturing method of the disposable wearing article 1B of the second embodiment will now be described in points different from the manufacturing method of the disposable wearing article 1A of the first embodiment.

In the step of manufacturing the first elastic laminated body 12A on the front portion P side and the second elastic laminated body 12B on the back portion Q side in a transverse flow state (see Steps 1 through 5 of FIG. 1), the outer surface web 10 that is made of non-woven fabric and fed continuously in the length direction A is cut in the length direction A using the slitter 16 (see a cutting line D). Cut first outer surface web 10A and second outer surface web 10B are widened by a specific interval W6 in the width direction W.

Also, the inner surface web 11 that is made of non-woven fabric and fed continuously in the length direction A is cut in the length direction A using the S-cutter 15 so that the concave portions 12a and the convex portions 12b appear alternately (so-called S-cutting, see the cutting line C). Cut first inner surface web 11A and second inner surface web 11B are widened by a specific interval W6 in the width direction W, and are shifted in the length direction A by a phase matching device 13 so that the concave portions 12b of the respective webs 11A and 11B oppose each other.

The phase matching can be performed after the first outer surface web 10A and the first inner surface web 11A are bonded, after the second outer surface web 10B and the second inner surface web 11B are bonded (see Step 1 of FIG. 1), or after the portion 12c where contractive forces are lessened is formed (see Step 2 of FIG. 1). In other words, the phase matching can be performed at any timing from the widening step to the bonding step of the absorber 3. However, when it is performed after the bonding step, both the webs 10A and 11A and the webs 10B and 11B become firm, they can be handled more readily. It should be noted, however, that the phase matching can be omitted as in the first embodiment.

Subsequently, the first elastic laminated body 12A on the front portion P side and the second elastic laminated body 12B on the back portion Q side are manufactured by bonding the first outer surface web 10A to the first inner surface web 11A and the second outer surface web 10B to the second inner surface web 11B, all of which are cut and widened, while inserting the body-fitting elastic members 4 on the front portion P side and the back portion Q side in an extended state in the length direction A in between. The second outer surface web 10B and the second inner surface web 11B may be bonded while inserting the leg peripheral elastic member 5B in between.

Meanwhile, in the step of fabricating the disposable wearing article 1B in a transverse flow state (see Steps 11 through 16 of FIG. 1), the absorber 3 is bonded across the portion 12c where contractive forces at the convex portions 12b of the inner surface webs 11 in the first elastic laminated body 12A and the second elastic laminated body 12B are lessened.

Subsequently, the leg hole portions S are formed by cutting out the outer surface web 10 using a trim cutter 22 provided between Step 12 and Step 13.

In this embodiment, the outer surface web 10 alone is cut out using the trim cutter 22. However, the inner surface web 11 may be cut out as well, or alternatively, the both edge portions of the absorber 3 may be cut off together with the outer surface web 10 and the inner surface web 11.

According to the manufacturing method of the disposable wearing article 1B of the second embodiment, the outer surface web 10 is cut in the length direction A, and the cut first outer surface web 10A and second outer surface web 10B are widened. Meanwhile, the inner surface web 11 is cut in the length direction A so that the concave portions 12a and the convex portions 12b appear alternately, and the cut first inner surface web 11A and second inner surface web 11B are widened followed by the phase matching. After the first elastic laminated body 12A and the second elastic laminated body 12B are manufactured by bonding the first outer surface web 10A to the first inner surface web 11A and the second outer surface web 10B to the second inner surface web 11B while inserting the body-fitting elastic members 4 in between, the absorber 3 is bonded to bridge between the convex portions 12b of the first inner surface web 11A and the second inner surface web 11B.

The outer surface web 10 is therefore in a seamless state in the constant width in the width direction, and transported in open width while tension in the length direction is kept applied. The outer surface web 10 therefore has a resistance against contraction of the body-fitting member 4 inserted between the self and the inner surface web 11. Hence, the occurrence of wrinkles in the convex portions 12b of the manufactured first elastic laminated body 12A and second elastic laminated body 12B can be suppressed in comparison with a case where both the outer surface web 10 and the inner surface web 11 have the concave portion and the convex portion. It is thus possible to avoid a problem attributed to the occurrence of wrinkles when the absorber 3 is attached to bridge between the convex portions 12b of the first inner surface web 11A and the second inner surface web 11B.

The method of the invention is particularly effective in a case where the wrinkles and/or creases are readily produced as described above, for example, when the leg peripheral elastic member 5B is inserted in the convex portion 12b.

In addition, because the cover sheet 2 used in the first embodiment can be omitted, the cost can be saved.

Further, by shifting the cut first inner surface web 11A and second inner surface web 11B in the length direction so that the convex portions 12b of the respective webs 11A and 11B oppose each other, it is possible to bond the absorber 3 to bridge between the convex portions 12b of the first elastic laminated body 12A and the second elastic laminated body 12B. This configuration makes it possible to bond the absorber 3 to the convex portions 12b of a large space, which enables the bonding to be performed in a reliable manner.

In addition, because part of the absorber 3 can be covered with the convex portions 12b of both the first elastic laminated body 12A and the second elastic laminated body 12B, the wearing article can be approximated to underpants in shape. The visual quality can be therefore improved, which can in turn increase the commercial value of the disposable wearing article 1B.

Third Embodiment

Figure 18:
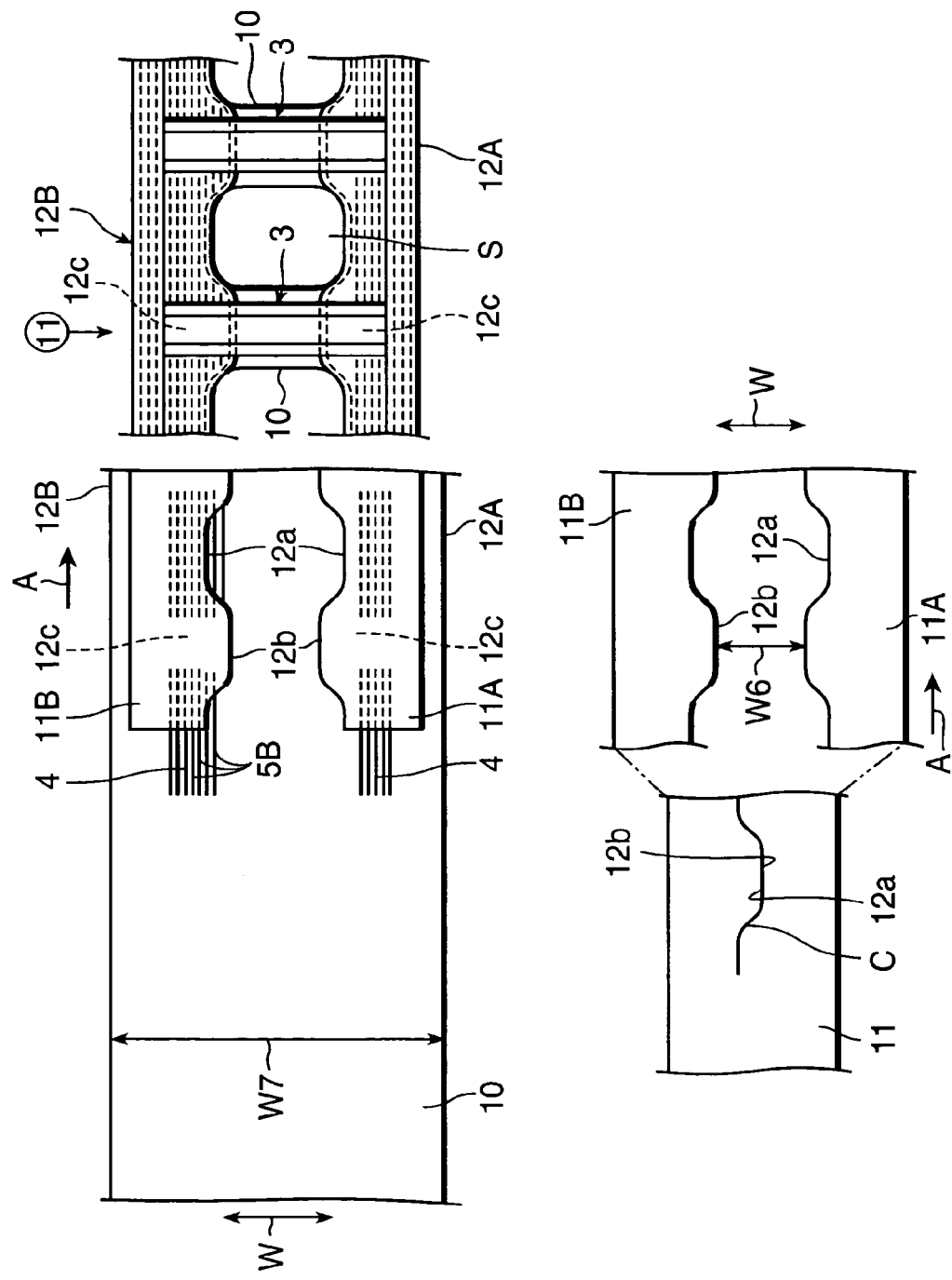
FIG. 18 is a plan view showing a manufacturing status in major steps of a disposable wearing article of a third embodiment.

FIG. 18 and FIG. 19 show a manufacturing method of a disposable wearing article 1C of the third embodiment.

In comparison with the disposable wearing article 1B of the second embodiment, the disposable wearing article 1C of the third embodiment is different in that the outer surface web 10 is neither cut nor widened.

The manufacturing method of the disposable wearing article 1C of the third embodiment will now be described in points different from the manufacturing method of the disposable wearing article 1B of the second embodiment.

Referring to FIG. 15 of the second embodiment again, the step of cutting and widening the outer surface web 10 (see a portion indicated by a capital F) and the step of bonding the film 9b of the back sheet 9B (see a portion indicated by a capital G) can be omitted.

In other words, the inner surface web 11 that is made of non-woven fabric and fed continuously in the length direction A is cut in the length direction A using the S-cutter 15 so that the concave portions 12a and the convex portions 12b appear alternately (so-called S-cutting, see the cutting line C), and the cut first inner surface web 11A and second inner surface web 11B are widened by a specific interval W6 in the width direction W while being shifted in the length direction A by the phase matching device 13 so that the convex portions 12b of the respective webs 11A and 11B oppose each other. It should be noted, however, that the phase matching can be omitted as in the first embodiment.

The outer surface web 10 that is made of non-woven fabric set to have a breadth W7 in a widened state and fed continuously in the length direction A is bonded to the first inner surface web 11A and the second inner surface web 11B while inserting the body-fitting elastic members 4 on the front portion P side and the back portion Q side in an extended state in the length direction A in between. The first elastic laminated body 12A on the front portion P side and the second elastic laminated body 12B on the back portion Q side are thus manufactured while being connected via the outer surface web 10. The outer surface web 10 may be bonded to the second inner surface web 11B while inserting the leg peripheral elastic member 5B in between.

Meanwhile, in the step of fabricating the disposable wearing article 1C in a transverse flow state (see Steps 11 through 16 of FIG. 1), the absorber 3 is bonded not only across the portion 12c where contractive forces at the convex portions 12b of the inner surface webs 11 in the first elastic laminated body 12A and the second elastic laminated body 12B are lessened, but also onto the seamless outer surface web 10.

Subsequently, the leg hole portions S are formed by cutting out the outer surface web 10 using the trim cutter 22 provided between Step 12 and Step 13.

In this embodiment, the outer surface web 10 alone is cut out using the trim cutter 22. However, the inner surface web 11 may be cut out as well, or alternatively, the both edge portions of the absorber 3 may be cut off together with the outer surface web 10 and the inner surface web 11.

According to the manufacturing method of the disposable wearing article 1C of the third embodiment, the inner surface web 11 is cut in the length direction A so that the concave portions 12a and the convex portions 12b appear alternately, and the cut first inner surface web 11A and second inner surface web 11B are widened. Meanwhile, after the first elastic laminated body 12A and the second elastic laminated body 12B connected via the outer surface web 10 are manufactured by bonding the outer surface web 10 that is set to have the breadth W7 in a widened state is bonded to the first inner surface web 11A and to the second inner surface web 11B while inserting the body-fitting elastic members 4 in between, the absorber 3 is bonded to bridge between the convex portions 12b of the first inner surface web 11A and the second inner surface web 11B.

The outer surface web 10 is therefore neither cut nor widened, and transported in open width while tension in the length direction is kept applied. The outer surface web 10 thus has a resistance against the contraction of the body-fitting elastic members 4 inserted between the self and the inner surface web 11. It is thus possible to avoid a problem attributed to the occurrence of wrinkles and arising when the absorber is attached to bridge between the convex portions 12b of the first inner surface web 11A and the second inner surface web 11B.

When the absorber 3 is bonded to bridge between the first inner surface web 11A and the second inner surface web 11B that are cut and widened, trim losses in the webs 10 and 11 are hardly produced during the manufacturing steps. It is thus possible to reduce the manufacturing costs of the disposable wearing article 1C.

The method of the invention is particularly effective in a case where the wrinkles and/or creases are readily produced as described above, for example, when the leg peripheral elastic member 5B is inserted in the convex portion 12b.

Further, because the cover sheet 2 used in the first embodiment can be omitted, the cost can be saved.

Furthermore, because the intermediate portion of the absorber 3 can be covered with the seamless outer surface web 10, the visual quality is increased.

Fourth Embodiment

FIG. 20 through FIG. 24 show a manufacturing method of a disposable wearing article 1D of a fourth embodiment.

In comparison with the disposable wearing article 1B of the second embodiment, the disposable wearing article 1D of the fourth embodiment is different in that the inner surface web is not S-cut.

The manufacturing method of the disposable wearing article 1D of the fourth embodiment will now be described in points different from the manufacturing method of the disposable wearing article 1B of the second embodiment.

Figure 20:
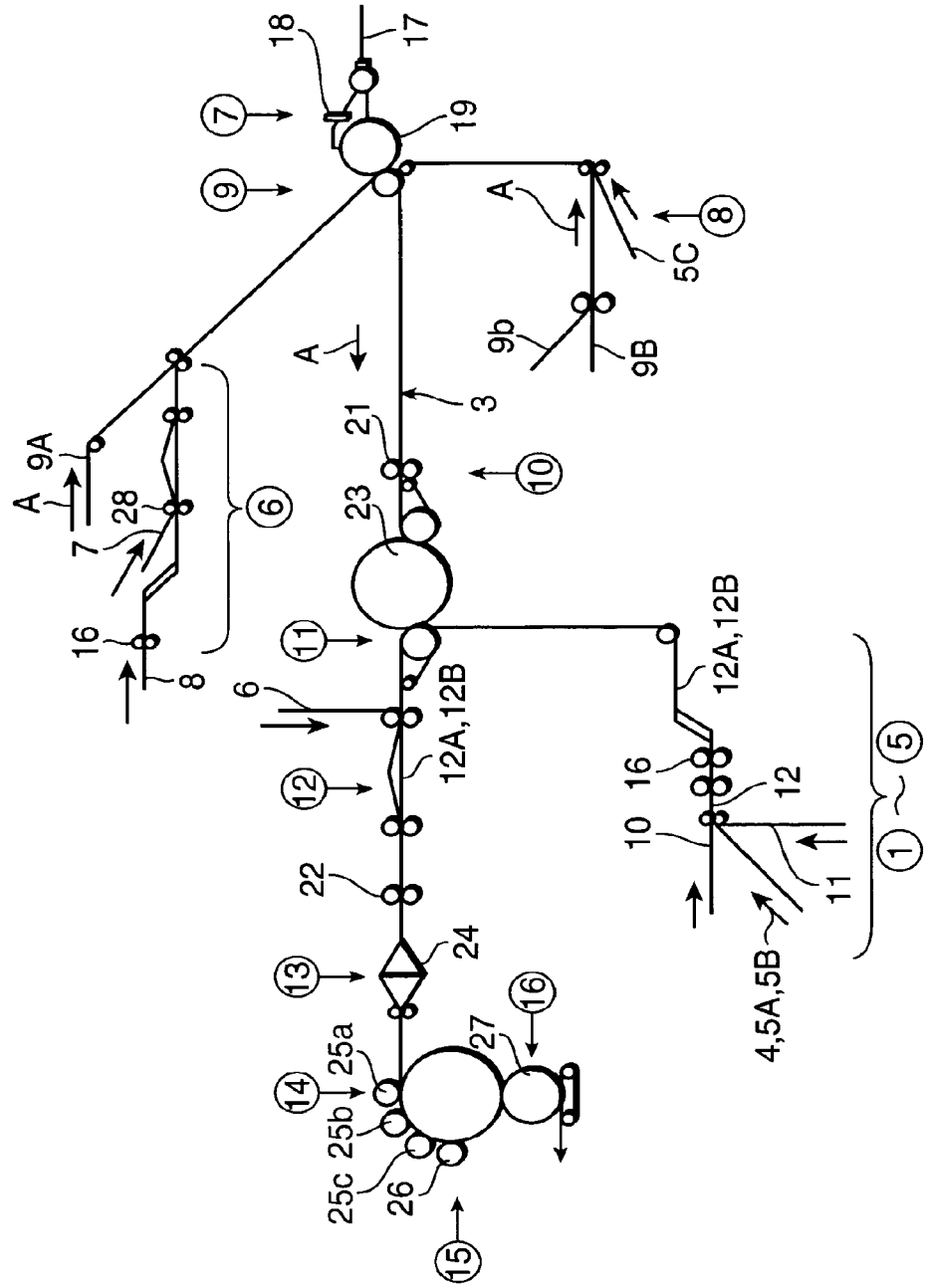
FIG. 20 is a system view detailing the manufacturing steps of a disposable wearing article of a fourth embodiment.
Figure 21:
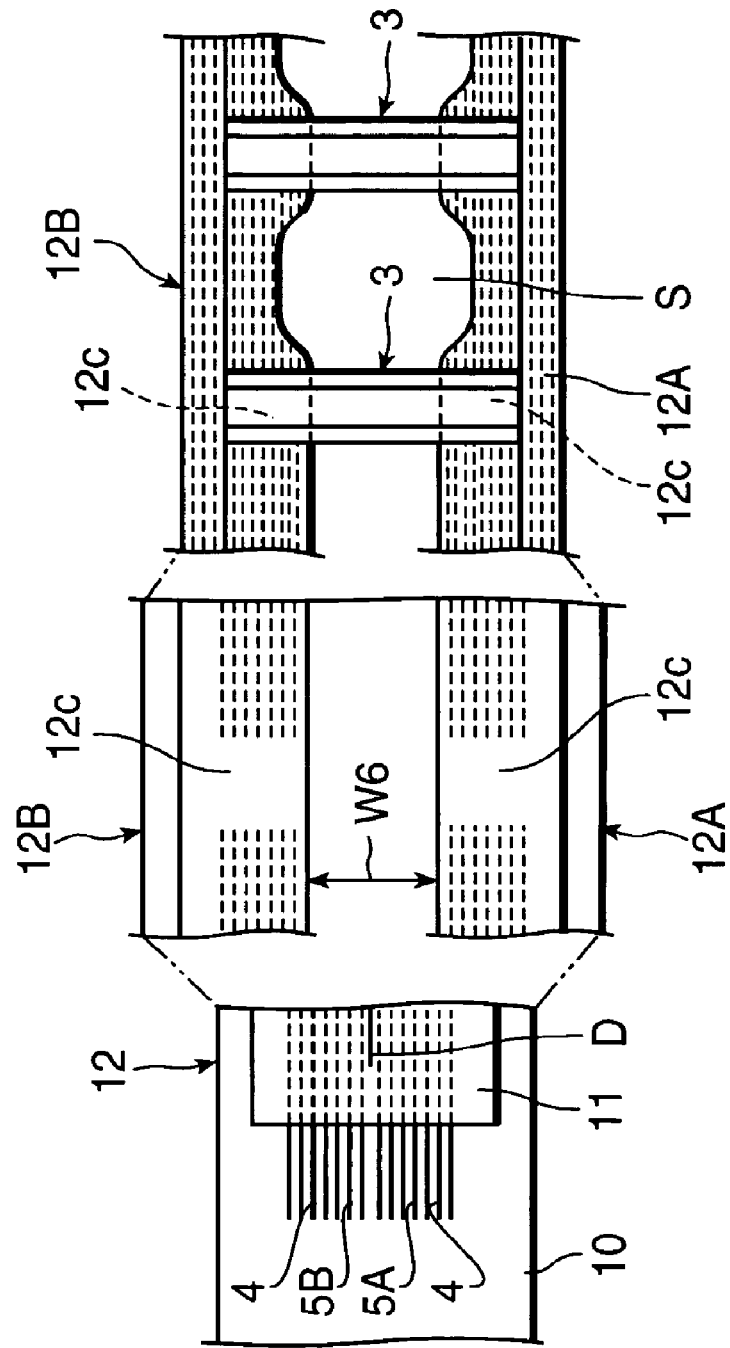
FIG. 21 is a plan view showing a manufacturing status in major steps.
Figure 22A:
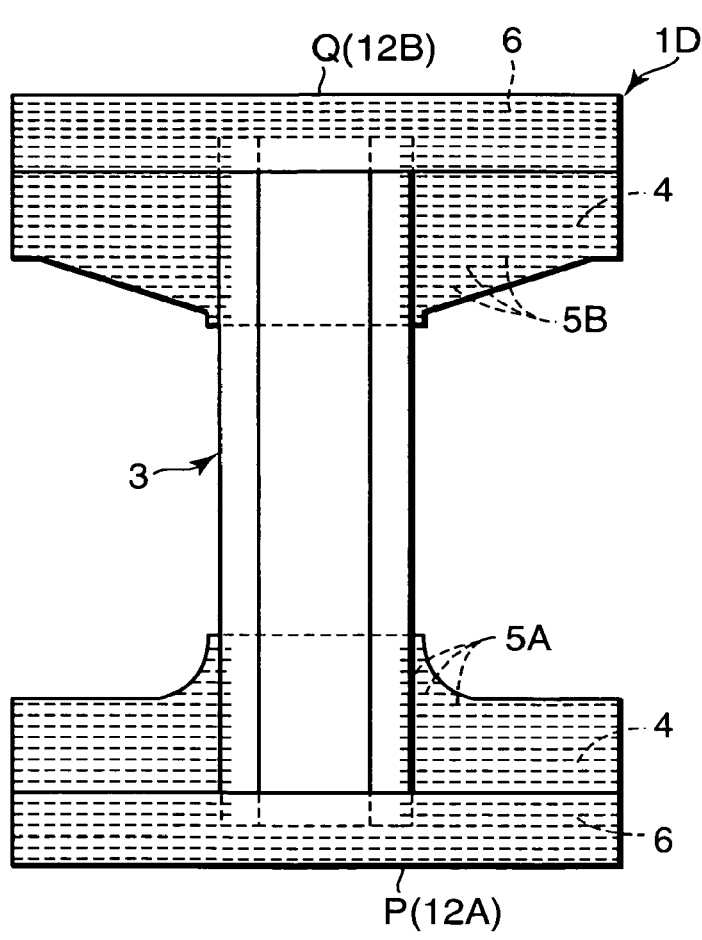
FIG. 22 shows a disposable wearing article of the fourth embodiment, FIG. 22A being a plan view in a developed state and FIG. 22B being a schematic sectional side elevation.
Figure 22B:
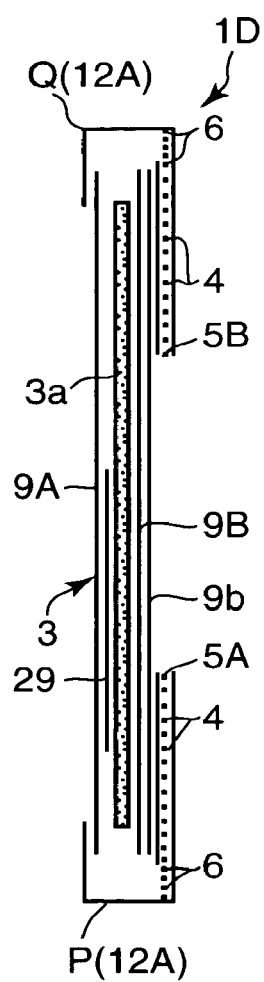

As are shown in FIG. 20 through FIG. 22, in the step of manufacturing the first elastic laminated body 12A on the front portion P side and the second elastic laminated body 12B on the back Q side in a transverse flow state (see Steps 1 through 5 of FIG. 1), the elastic laminated body 12 is manufactured by bonding the outer surface web 10 and the inner surface web 11 that are fed continuously in the length direction A while inserting the body-fitting elastic members 4 and the leg peripheral elastic members 5A and 5B on the front portion P side and the back portion Q side in an extended state in the length direction A in between.

The elastic laminated body 12 is cut in the length direction A using the slitter 16 (see the cutting line D), and the cut first elastic laminated body 12A and second elastic laminated body 12B are widened by a specific interval W6 in the width direction W.

Meanwhile, in the step of fabricating the disposable wearing article 1C in a transverse flow state (see Steps 11 through 16 of FIG. 1), the absorber 3 is bonded across the portion 12c where contractive forces of the inner surface webs 11 in the first elastic laminated body 12A and the second elastic laminated body 12B are lessened.

Subsequently, the leg hole portions S are formed by cutting out the first elastic laminated body 12A and the second elastic laminated body 12B using the trim cutter 22 provided between Step 12 and Step 13. The both edge portions of the absorber 3 may be also cut off.

According to the manufacturing method of the disposable wearing article 1D of the fourth embodiment, the leg hole portions S are cut out after the absorber 3 is bonded to bridge between the widened first elastic laminated body 12A and second elastic laminated body 12B. The absorber 3 can be therefore provided in the absence of a problem attributed to occurrence of wrinkles as described above.

Figure 23A:
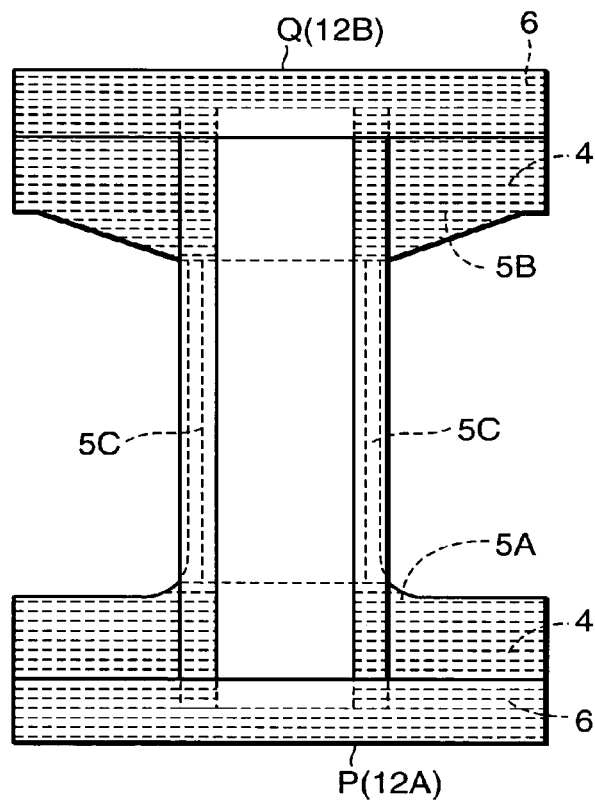
FIG. 23 shows a disposable wearing article of a first modification, FIG. 23A being a plan view in a developed state, FIG. 23B being a schematic sectional side elevation, and FIG. 23C being a schematic sectional front view.
Figure 23B:
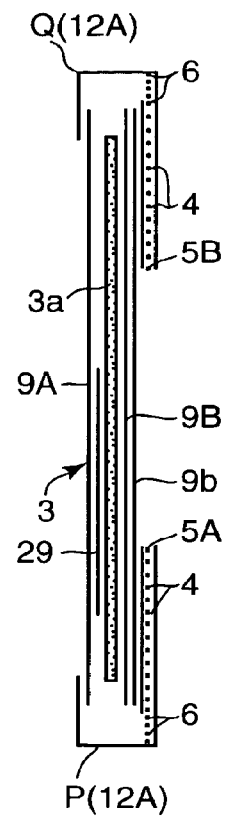
Figure 23C:
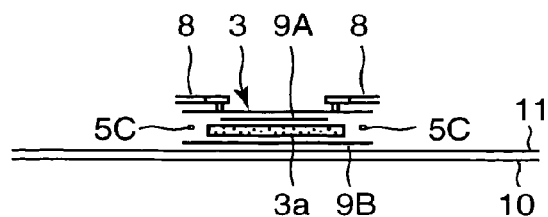
Figure 24:
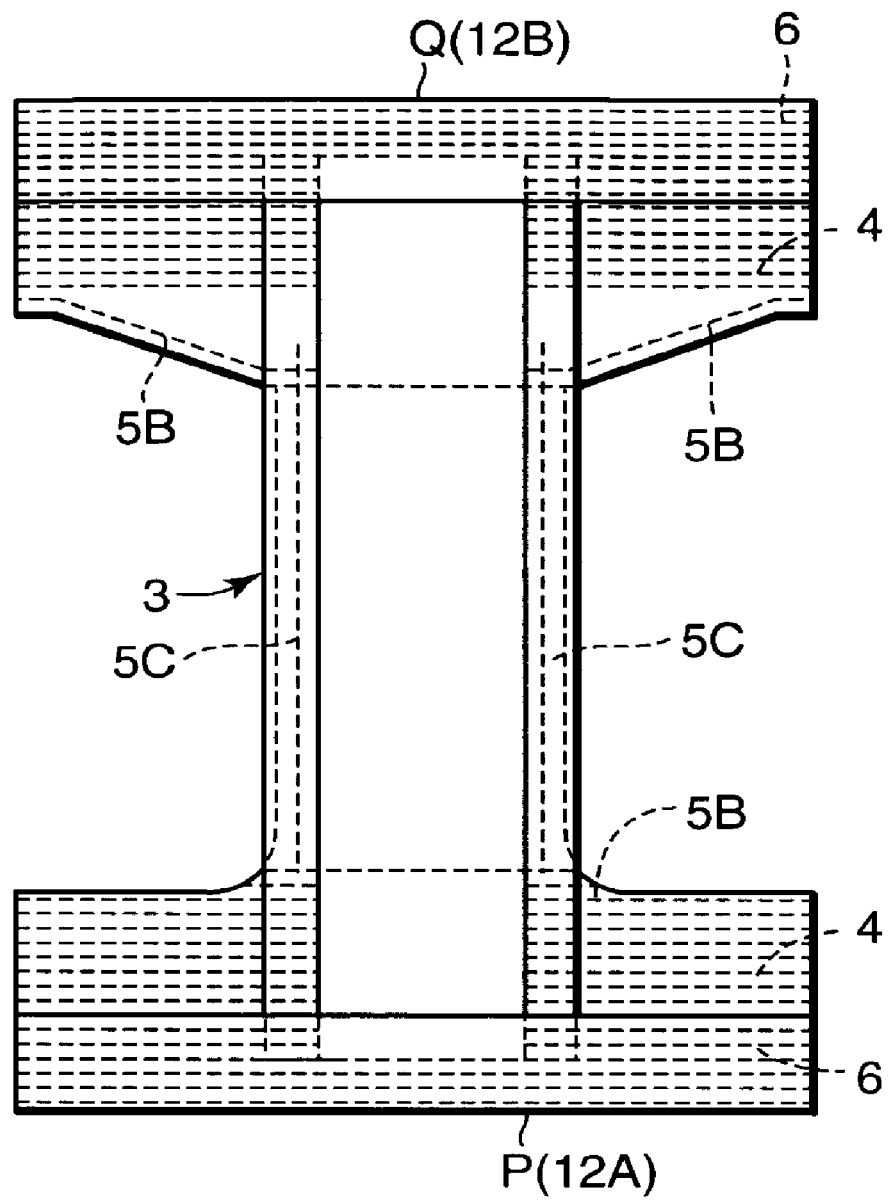
FIG. 24 is a plan view of a disposable wearing article of a second modification in a developed state.

As is shown in FIG. 23, leg peripheral elastic members 5C that cross with the leg peripheral elastic member 5A on the front portion P side and the leg peripheral elastic member 5B on the back portion Q side may be attached to the absorber 3. Also, as is shown in FIG. 24, the leg peripheral elastic member 5B on the back portion Q side may be attached in a curved line along the back edge portion of the back portion Q instead of being attached linearly.

Fifth Embodiment

Figure 25:
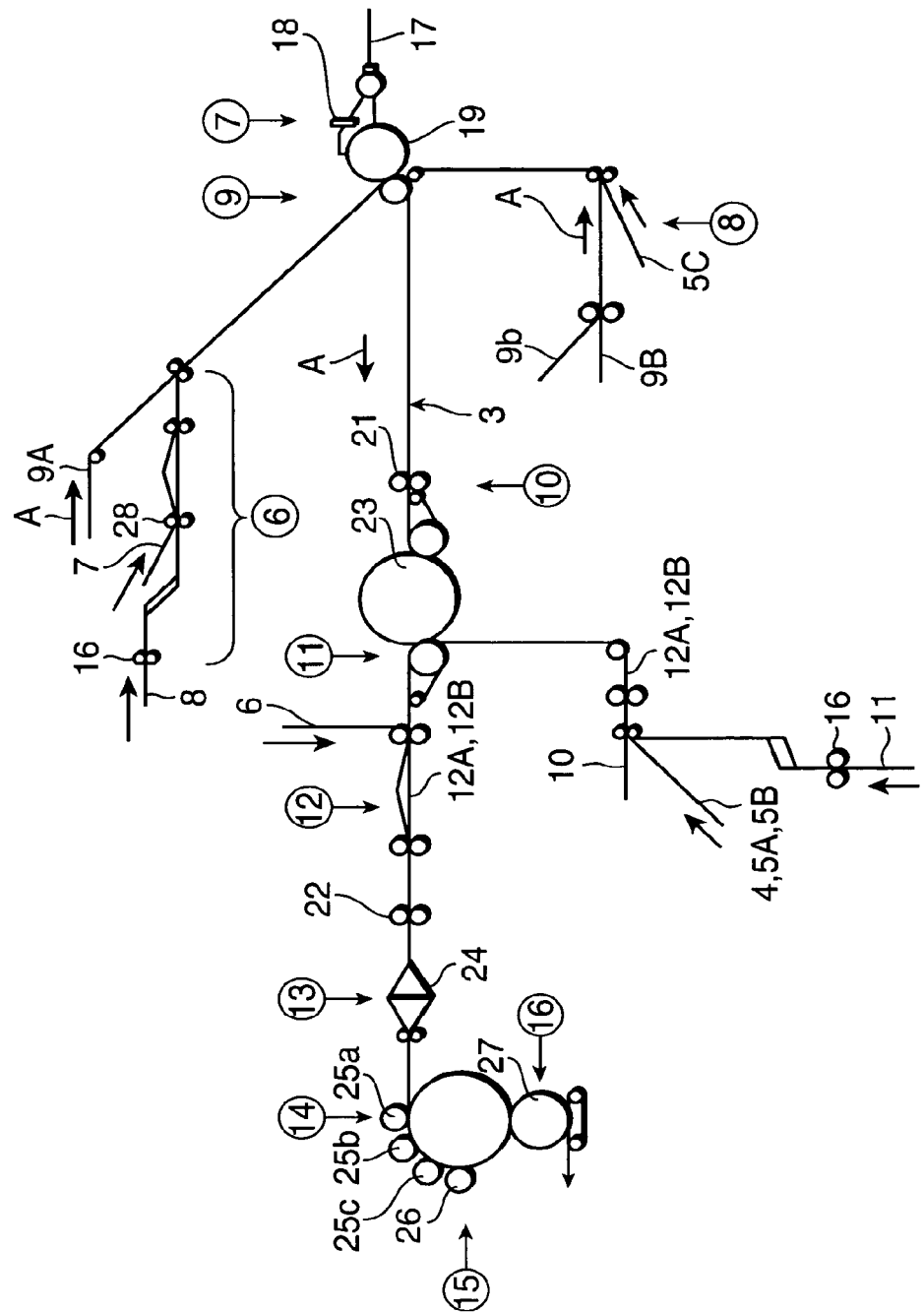
FIG. 25 is a system view detailing the manufacturing steps of a disposable wearing article of a fifth embodiment.
Figure 28:
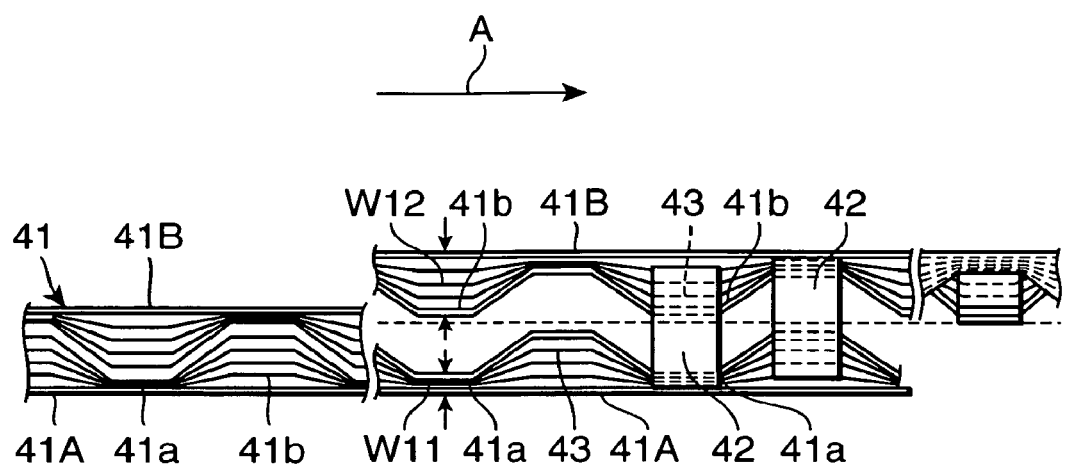
FIG. 28 is a plan view showing a manufacturing status in major steps of a disposable wearing article in the related art.

FIG. 25 through FIG. 27 show a manufacturing method of a disposable wearing article 1E of a fifth embodiment.

In comparison with the disposable wearing article 1B of the second embodiment, the disposable wearing article 1E of the fifth embodiment is different in that the inner surface web is not S-cut.

The manufacturing method of the disposable wearing article 1E of the fifth embodiment will now be described in points different from the manufacturing method of the disposable wearing article 1B of the second embodiment.

The inner surface web 11 that is made of non-woven fabric and fed continuously in the length direction A is cut in the length direction A (see the cutting line D) using the slitter 16, and the cut first inner surface web 11A and second inner surface web 11B are widened by a specific interval W6 in the width direction W.

The outer surface web 10 that is made of non-woven fabric set to have a breadth W7 in a widened state and fed continuously in the length direction A is bonded to the first inner surface web 11A and to the second inner surface web 11B while inserting the body-fitting elastic members 4 and the leg peripheral elastic members 5A and 5B on the front portion P side and the back portion Q side in an extended state in the length direction A in between. The first elastic laminated body 12A on the front portion P side and the second elastic laminated body 12B on the back portion Q side are thus manufactured while being connected via the outer surface web 10.

Meanwhile, in the step of fabricating the disposable wearing article 1E in a transverse flow state (see Steps 11 through 16 of FIG. 1), the absorber 3 is bonded not only across the portion 12c where contractive forces of the inner surface webs 11 in the first elastic laminated body 12A and the second elastic laminated body 12B are lessened, but also onto the seamless outer surface web 10.

Subsequently, the leg hole portions S are formed by cutting out the first elastic laminated body 12A and the second elastic laminated body 12B using the trim cutter 22 provided between Step 12 and Step 13. The both edge portions 3b of the absorber 3 are also cut off using the trim cutter 22 in this embodiment.

According to the manufacturing method of the disposable wearing article 1E of the fifth embodiment, the leg hole portions S are cut out after the absorber 3 is bonded to bridge between the first elastic laminated body 12A and second elastic laminated body 12B connected via the outer surface web 10. The absorber 3 can be therefore provided in the absence of a problem attributed to the occurrence of wrinkles as described above.

As described above, a first manufacturing method comprises steps of: cutting a web in a length direction so that a concave portion and a convex portion appear alternately; attaching a cover sheet to bridge between cut first web and second web; widening the first web and the second web to which the cover sheet is attached; and attaching an absorber onto the cover sheet.

According to the first manufacturing method, the web is cut in the length direction so that the concave portion and the convex portion appear alternately, and the cover sheet is attached to bridge between the cut first web and second web, after which the first web and the second web are widened. The absorber is then attached onto the cover sheet.

By attaching the cover sheet to bridge between the first web and the second web not after the widening when wrinkles are readily produced, but before the widening when wrinkles are not readily produced, preferably, after the cutting when wrinkles are hardly produced, and more preferably, immediately after the cutting, the occurrence of wrinkles particularly in the convex portion can be eliminated. It is thus possible to avoid a problem attributed to wrinkles and arising when the absorber is attached.

A second manufacturing method comprises steps of: manufacturing an elastic laminated body by laminating two webs while inserting an elastic member in an extended state in a web length direction in between; cutting the elastic laminated body in a length direction so that a concave portion and a convex portion appear alternately; attaching a cover sheet to bridge between the concave portion and the convex portion of cut first elastic laminated body and second elastic laminated body, respectively; widening the first elastic laminated body and the second elastic laminated body to which the cover sheet is attached; and attaching an absorber onto the cover sheet.

According to the second manufacturing method, after the elastic laminated body is manufactured by laminating the two webs while inserting the elastic member in between, the elastic laminated body is cut in the length direction so that the concave portion and the convex portion appear alternately. After the cover sheet is attached to bridge between the concave portion and the convex portion of the cut first elastic laminated body and second elastic laminated body, respectively, the first elastic laminated body and the second elastic laminated body are widened. The absorber is then attached onto the cover sheet.

By attaching the cover sheet to bridge between a first belt member and a second belt member not after the widening when wrinkles are readily produced, but before the widening when wrinkles are not readily produced, preferably, after the cutting when wrinkles are hardly produced, and more preferably, immediately after the cutting, it is possible to avoid a problem attributed to wrinkles and arising when the absorber is attached.

Further, this method is particularly effective in a case where a leg peripheral elastic member is inserted in the convex portion, because the occurrence of wrinkles or creases can be suppressed as much as possible.

In the first and second manufacturing method, it is preferable that the cover sheet is provided with slack comparable to widening when attached to bridge between the webs or between the concave and convex portions.

When the cover sheet is attached to bridge between the webs or between the concave and convex portions with slack comparable to the widening, the attachment can be performed with ease.

A third manufacturing method comprises steps of: cutting an outer surface web in a length direction; widening cut first outer surface web and second outer surface web; cutting an inner surface web in a length direction so that a concave portion and a convex portion appear alternately; widening cut first inner surface web and second inner surface web; manufacturing a first elastic laminated body and a second elastic laminated body by laminating the first outer surface web to the first inner surface web and the second outer surface web to the second inner surface web while inserting an elastic member in an extended state in a web length direction in between; and attaching an absorber to bridge between the first inner surface web and the second inner surface web.

According to the third manufacturing method, the outer surface web is cut in the length direction and the cut first outer surface web and second outer surface web are widened. Meanwhile, the inner surface web is cut in the length direction so that the concave portion and the convex portion appear alternately, and the cut first inner surface web and second inner surface web are widened. After the first elastic laminated body and the second elastic laminated body are manufactured by laminating the first outer surface web to the first inner surface web and the second outer surface web to the second inner surface web while inserting the elastic member in between, the absorber is attached to bridge between the first inner surface web and the second inner surface web.

The outer surface web is therefore in a seamless state in the constant width in the width direction, and transported in open width while tension in the length direction is kept applied. The outer surface web thus has a resistance against contraction of the elastic member inserted between the self and the inner surface web. Hence, the occurrence of wrinkles in the first elastic laminated body and the second elastic laminated body thus manufactured can be suppressed in comparison with a case where both the outer surface web and the inner surface web have the concave portions and the convex portions. It is thus possible to avoid a problem attributed to the occurrence of wrinkles and arising when the absorber is attached to bridge between the convex portions of the first inner surface web and the second inner surface web.

Further, this method is particularly effective in a case where a leg peripheral elastic member is inserted in the convex portion, because the occurrence of wrinkles or creases can be suppressed as much as possible.

A fourth manufacturing method comprises steps of: cutting an inner surface web in a length direction so that a concave portion and a convex portion appear alternately; widening cut first inner surface web and second inner surface web; laminating an outer surface web to the first inner surface web and to the second inner surface web while inserting an elastic member in an extended state in a web length direction in between; and attaching an absorber to bridge between the first inner surface web and the second inner surface web.

According to the fourth manufacturing method, the inner surface web is cut in the length direction so that the concave portion and the convex portion appear alternately, and the cut first inner surface web and second inner surface web are widened. After the first elastic laminated body and the second elastic laminated body are manufactured by laminating the outer surface web to the first inner surface web and to the second inner surface web while inserting the elastic member in between, the absorber is attached to bridge between the first inner surface web and the second inner surface web.

The outer surface web is therefore neither cut nor widened, and transported in open width while tension in the length direction is kept applied. The outer surface web thus has a resistance against contraction of the elastic member inserted between the self and the inner surface web. It is thus possible to avoid a problem attributed to the occurrence of wrinkles and arising when the absorber is attached to bridge between the convex portions of the first inner surface web and the second inner surface web.

In addition, because the intermediate portion of the absorber can be covered with the seamless outer surface web, the visual quality can be improved.

The third and fourth manufacturing methods may be preferably configured to further include a step of shifting the cut first inner surface web and second inner surface web in the length direction so that concave portions of the respective webs oppose each other.

By shifting the cut first inner surface web and second inner surface web in the length direction so that the convex portions of the respective webs oppose each other in this manner, the absorber can be attached to bridge between the convex portions of both the first elastic laminated body and the second elastic laminated body. This enables the absorber to be attached to the convex portions of a large space. The attachment can be therefore performed in a reliable manner.

In addition, because part of the absorber can be covered with the convex portions of both the first elastic laminated body and the second elastic laminated body, the wearing article can be approximated to underpants in shape. The visual quality can be therefore improved, which can in turn increase the commercial value of the wearing article.

The first through fourth manufacturing methods may be preferably configured in such a manner that the elastic member includes a waist elastic member, a body-fitting elastic member, and a leg peripheral elastic member, and that the leg peripheral elastic member is in a state where the leg peripheral elastic member is provided in a linear state or a curved line state in a width direction or in a state having the both states.

When configured in this manner, it is possible to prevent the wearing article put on a wearer from drooping down by the waist elastic member, while the wearing article can be fit to the body by the body-fitting elastic member and adhesion to the leg portions can be enhanced by the leg peripheral elastic member.

It may be preferable that the first through fourth manufacturing methods further include a step of side-sealing both side portions of the first web and the second web or both side portions of the first elastic laminated body and the second elastic laminated body while the absorber is in a folded state.

By side-sealing the both side portions of the first web and the second web or the both side portions of the first elastic laminated body and the second elastic laminated body while the absorber is in a folded state, a wearing article of an underpants type can be obtained.

It may be preferable that the first through fourth manufacturing methods further include a step of forming leg hole portions.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds are therefore intended to embraced by the claims.

What is claimed is:

1. A method for manufacturing a disposable wearing article, comprising the steps of:
   cutting an outer surface web in a length direction of the outer surface web to form a first outer surface web having a constant width in a width direction of the first outer surface web and a second outer surface web having a constant width in a width direction of the second outer surface web;
   spacing the first outer surface web and the second outer surface web from each other;
   cutting an inner surface web in a length direction of the inner surface web to form a first inner surface web and a second inner surface web;
   spacing the first inner surface web and the second inner surface web from each other;
   manufacturing a first elastic laminated body by laminating the first outer surface web to the first inner surface web so as to define a first end portion on the first outer surface web, the first end portion protruding outwardly beyond a side edge of the first inner surface web in a width direction of the first elastic laminated body, while placing a first body-fitting elastic member in an extended state in a web length direction between the first outer surface web and the first inner surface web after the first outer surface web and the first inner surface web have been separated respectively from the second outer surface web and the second inner surface web;
   manufacturing a second elastic laminated body by laminating the second outer surface web to the second inner surface web so as to define a second end portion on the second outer surface web, the second end portion protruding outwardly beyond a side edge of the second inner surface web in a width direction of the second elastic laminated body, while placing a second body-fitting elastic member in an extended state in a web length direction between the second outer surface web and the second inner surface web after the second outer surface web and the second inner surface web have been separated respectively from the first outer surface web and the first inner surface web;
   attaching an absorber to the first elastic laminated body and the second elastic laminated body which are spaced from each other;
   placing a first waist elastic member upon the first end portion and a second waist elastic member upon the second end portion; and
   folding the first end portion inward to thereby enclose the first waist elastic member therein and folding the second end portion inward to thereby enclose the second waist elastic member therein after the step of manufacturing the first elastic laminated body and the second elastic laminated body.

2. The method for manufacturing a disposable wearing article according to claim 1, wherein:
   in the steps of cutting the inner surface web, the inner surface web is cut to thereby have concave portions and convex portions alternately.

3. The method for manufacturing a disposable wearing article according to claim 2, further comprising:
a step of shifting the first inner surface web and the second inner surface web in the length direction so that concave portions of the respective webs oppose each other.

4. The method for manufacturing a disposable wearing article according to claim 1, further comprising:
a step of forming a leg hole portion by cutting out the first and second outer surface webs after the steps of manufacturing the first elastic laminated body and the second elastic laminated body.

5. The method for manufacturing a disposable wearing article according to claim 1, further comprising
a step of side-sealing both side portions of the first elastic laminated body and the second elastic laminated body while the absorber is in a folded state.

6. A method for manufacturing a disposable wearing article, comprising the steps of:
cutting an inner surface web in a length direction of the inner surface web into a first inner surface web and a second inner surface web;
spacing the first inner surface web and the second inner surface web from each other;
manufacturing a first elastic laminated body and a second elastic laminated body by laminating a single outer surface web over the first inner surface web and the second inner surface web, the first elastic laminated body and the second elastic laminated body being connected via the single outer surface web, while placing a first body-fitting elastic member in an extended state in a web length direction between the single outer surface web and the first inner surface web and placing a second body-fitting elastic member in an extended state in a web length direction between the single outer web and the second inner surface web after spacing the first inner surface web and the second inner surface web from each other; and
forming a first portion where a contractive force of the first body-fitting elastic member is lessened in the first elastic laminated body after the step of manufacturing the first elastic laminated body and the second elastic laminated body;
forming a second portion where a contractive force of the second body-fitting elastic member is lessened in the second elastic laminated body, the first portion and the second portion being arranged in a width direction of the single outer surface web after the step of manufacturing the first elastic laminated body and the second elastic laminated body;
attaching an absorber to the first inner surface web at the first portion and the second inner surface web at the second portion which are spaced from other, and attaching the absorber to the single outer surface web between the first portion and the second portion while tension in a web length direction is kept applied to the single outer surface web; and
forming a leg hole portion by cutting out the single outer surface web after the step of manufacturing the first elastic laminated body and the second elastic laminated body, wherein:
in the step of manufacturing the first elastic laminated body and the second elastic laminated body, the single outer surface web is laminated over the first inner surface web and the second inner surface web so as to define a first end portion and a second end portion on the single outer surface web protruding outwardly beyond a side edge of the first inner surface web and a side edge of the second inner surface web in a width direction of the single outer surface web respectively,
the method further comprising:
placing a first waist elastic member upon the first end portion and a second waist elastic member upon the second end portion; and
folding the first end portion inward to thereby enclose the first waist elastic member therein and folding the second end portion inward to thereby enclose the second waist elastic member therein.

7. The method for manufacturing a disposable wearing article according to claim 6, wherein:
in the steps of cutting the inner surface web, the inner surface web is cut to thereby have concave portions and convex portions alternately.

8. The method for manufacturing a disposable wearing article according to claim 7, further comprising:
a step of shifting the first inner surface web and the second inner surface web in the length direction so that concave portions of the respective webs oppose each other.

9. The method for manufacturing a disposable wearing article according to claim 6, wherein:
in the step of cutting the inner surface web, the inner surface web is cut to form the first inner surface web having a constant width in a width direction and the second inner surface web having a constant width in a width direction.

10. The method for manufacturing a disposable wearing article according to claim 6, wherein:
the elastic member includes a waist elastic member, a body-fitting elastic member, and a leg peripheral elastic member, and the leg peripheral elastic member is in a state where the leg peripheral elastic member is provided inn a linear state or a curved line state in a width direction of the wearing article or in a state having the both states.

11. The method for manufacturing a disposable wearing article according to claim 6, further comprising:
a step of side-sealing both side portions of the first elastic laminated body and the second elastic laminated body while the absorber is in a folded state.

12. A method for manufacturing a disposable wearing article, comprising the steps of:
manufacturing an elastic laminated body by laminating an inner surface web and an outer surface web while placing a body-fitting elastic member in an extended state in a web length direction between the inner surface web and the outer surface web, the outer surface web having a greater width than the inner surface web, and a first end portion and a second end portion protruding outwardly beyond a first side edge and a second side edge of the inner surface web in a width direction of the elastic laminated body respectively;
cutting the elastic laminated body in a length direction of the elastic laminated body into a first elastic laminated body having a constant width in a width direction of the first elastic laminated body and a second elastic laminated body having a constant width in a width direction of the second elastic laminated body;
attaching an absorber to the first elastic laminated body and the second elastic laminated body;
placing a first waist elastic member upon the first end portion and a second waist elastic member upon the second end portion;
folding the first end portion inward to thereby enclose the first waist elastic member therein and folding the second end portion inward to thereby enclose the second waist elastic member therein after the step of manufacturing the elastic laminated body; and forming a leg hole portion by cutting out the first elastic laminated body and the second elastic laminated body.

13. The method for manufacturing a disposable wearing article according to claim 12, wherein: the first elastic laminated body and the second elastic laminated body are cut out after the step of attaching the absorber to the first elastic laminated body and the second elastic laminated body.

* * * * *